(12) United States Patent
Powell et al.

(10) Patent No.: US 12,642,785 B2
(45) Date of Patent: **\*Jun. 2, 2026**

(54) FORMULATIONS OF DIHYDROMYRICETIN AND A PERMEABILIZER

(71) Applicants: The Trustees of Princeton University, Princeton, NJ (US); Cheers Health Inc., Houston, TX (US)

(72) Inventors: Brooks Powell, Houston, TX (US); Robert K. Prud'homme, Princeton, NJ (US); Nicholas Caggiano, Princeton, NJ (US); Chang Tian, Princeton, NJ (US)

(73) Assignees: The Trustees of Princeton University, Princeton, NJ (US); Cheers Health Inc., Houston, TX (US)

( \* ) Notice: Subject to any disclaimer, the term of this patent is extended or adjusted under 35 U.S.C. 154(b) by 0 days.

This patent is subject to a terminal disclaimer.

(21) Appl. No.: 17/618,884

(22) PCT Filed: Jun. 12, 2020

(86) PCT No.: PCT/US2020/037542
§ 371 (c)(1),
(2) Date: Dec. 13, 2021

(87) PCT Pub. No.: WO2020/252346
PCT Pub. Date: Dec. 17, 2020

(65) Prior Publication Data
US 2022/0265600 A1 Aug. 25, 2022

Related U.S. Application Data

(60) Provisional application No. 62/861,895, filed on Jun. 14, 2019.

(51) Int. Cl.
*A61K 31/352* (2006.01)
*A61K 9/48* (2006.01)
(Continued)

(52) U.S. Cl.
CPC .......... *A61K 31/352* (2013.01); *A61K 9/4825* (2013.01); *A61K 47/12* (2013.01);
(Continued)

(58) Field of Classification Search
None
See application file for complete search history.

(56) References Cited

U.S. PATENT DOCUMENTS

| 1,690,760 A | 11/1928 | Volwiler |
|---|---|---|
| 3,239,370 A | 3/1966 | Thomson et al. |
(Continued)

FOREIGN PATENT DOCUMENTS

| CA | 1236009 | 5/1988 |
|---|---|---|
| CN | 1293825 C | 1/2007 |
(Continued)

OTHER PUBLICATIONS

Maher et al., Safety and efficacy of sodium caprate in promoting oral drug absorption: from in vitro to the clinic, 2009, Advanced Drug Delivery Reviews, 61(15), 17, 1427-1449, DOI: 10.1016/j.addr.2009.09.006 (Year: 2009).\*
(Continued)

*Primary Examiner* — David J Blanchard
*Assistant Examiner* — Lori K Mattison
(74) *Attorney, Agent, or Firm* — Nixon & Vanderhye P.C.; Lars H. Genieser

(57) ABSTRACT
Formulations including dihydromyricetin (DHM) and a fatty acid salt or a fatty acid.

10 Claims, 5 Drawing Sheets

━■━ Non-Enteric High Caprate

(51) Int. Cl.
     *A61K 47/12*        (2006.01)
     *A61K 47/14*        (2017.01)
     *A61K 47/18*        (2017.01)
     *A61K 47/24*        (2006.01)
     *A61K 47/44*        (2017.01)
(52) U.S. Cl.
     CPC ............ *A61K 47/14* (2013.01); *A61K 47/183*
         (2013.01); *A61K 47/24* (2013.01); *A61K 47/44*
                                                   (2013.01)

(56)                  References Cited

U.S. PATENT DOCUMENTS

| | | | |
|---|---|---|---|
| 3,410,938 | A | 11/1968 | Schippers |
| 4,678,516 | A | 7/1987 | Alderman et al. |
| 4,695,464 | A | 9/1987 | Alderman |
| 5,152,923 | A | 10/1992 | Weder et al. |
| 5,851,579 | A | 12/1998 | Wu et al. |
| 6,274,150 | B1 | 8/2001 | Simonnet et al. |
| 6,291,013 | B1 | 9/2001 | Gibson |
| 6,335,022 | B1 | 1/2002 | Simonnet et al. |
| 6,375,960 | B1 | 4/2002 | Simonnet et al. |
| 6,413,527 | B1 | 7/2002 | Simonnet et al. |
| 6,488,963 | B1 | 12/2002 | McGinity et al. |
| 6,610,653 | B1 | 8/2003 | Backstrom et al. |
| 6,689,371 | B1 | 2/2004 | Simonnet et al. |
| 6,730,322 | B1 | 5/2004 | Bernstein et al. |
| 6,763,607 | B2 | 7/2004 | Beyerinck et al. |
| 6,902,737 | B2 | 6/2005 | Quemin |
| 6,998,426 | B2 | 2/2006 | L'Alloret |
| 7,052,719 | B2 | 5/2006 | Bernstein |
| 7,842,308 | B2 | 11/2010 | McAllister et al. |
| 7,977,024 | B2 | 7/2011 | Zhou et al. |
| 8,137,699 | B2 | 3/2012 | Johnson et al. |
| 8,298,581 | B2 | 10/2012 | Fischer et al. |
| 8,486,423 | B2 | 7/2013 | Brough et al. |
| 8,603,514 | B2 | 12/2013 | Yang |
| 8,623,329 | B1 | 1/2014 | Hansen et al. |
| 8,703,196 | B2 | 4/2014 | Babcock et al. |
| 9,504,658 | B2 | 11/2016 | Miller et al. |
| 9,603,830 | B2 | 3/2017 | Powell |
| 10,231,937 | B2 | 3/2019 | Pagels et al. |
| 10,786,522 | B2 | 9/2020 | Burgos et al. |
| 11,103,461 | B2 | 8/2021 | Prud'Homme et al. |
| 12,343,324 | B2 | 7/2025 | Prud'Homme et al. |
| 2001/0044474 | A1 | 11/2001 | Curatolo et al. |
| 2003/0049311 | A1 | 3/2003 | MacAllister et al. |
| 2003/0054037 | A1 | 3/2003 | Babcock et al. |
| 2003/0104063 | A1 | 6/2003 | Babcock et al. |
| 2003/0163931 | A1 | 9/2003 | Beyerinck et al. |
| 2003/0170309 | A1 | 9/2003 | Babcock et al. |
| 2003/0185893 | A1 | 10/2003 | Beyerinck et al. |
| 2003/0228358 | A1 | 12/2003 | Perlman et al. |
| 2004/0052824 | A1 | 3/2004 | Chacra-Vernet |
| 2004/0091546 | A1 | 5/2004 | Johnson et al. |
| 2004/0115256 | A1 | 6/2004 | MacAllister et al. |
| 2004/0132771 | A1 | 7/2004 | Babcock et al. |
| 2004/0156905 | A1 | 8/2004 | Babcock et al. |
| 2004/0185112 | A1 | 9/2004 | Beyerinck et al. |
| 2004/0194338 | A1 | 10/2004 | Beyerinck et al. |
| 2006/0040831 | A1 | 2/2006 | Cassidy et al. |
| 2006/0057215 | A1 | 3/2006 | Raiche et al. |
| 2006/0224095 | A1 | 10/2006 | Claverie et al. |
| 2007/0231355 | A1 | 10/2007 | Quadir et al. |
| 2007/0281003 | A1 | 12/2007 | Fuisz et al. |
| 2008/0145432 | A1 | 6/2008 | Kakizawa et al. |
| 2008/0274194 | A1 | 11/2008 | Miller et al. |
| 2009/0053315 | A1 | 2/2009 | Brough et al. |
| 2009/0155326 | A1 | 6/2009 | Mack et al. |
| 2010/0166866 | A1 | 7/2010 | Fischer et al. |
| 2010/0305219 | A1 | 12/2010 | Granick et al. |
| 2010/0330368 | A1 | 12/2010 | Prud'homme et al. |
| 2011/0022129 | A1 | 1/2011 | Prud'homme et al. |
| 2011/0064821 | A1 | 3/2011 | Catchpole et al. |
| 2011/0206739 | A1 | 8/2011 | Nicolosi et al. |

| | | | |
|---|---|---|---|
| 2011/0229516 | A1 | 9/2011 | Ochomogo et al. |
| 2012/0009267 | A1 | 1/2012 | Cho et al. |
| 2012/0121510 | A1 | 5/2012 | Brem et al. |
| 2012/0171254 | A1 | 7/2012 | Johnson et al. |
| 2013/0053435 | A1 | 2/2013 | Liang et al. |
| 2013/0064954 | A1 | 3/2013 | Ochomogo et al. |
| 2013/0337078 | A1 | 12/2013 | Mayer et al. |
| 2013/0337096 | A1 | 12/2013 | Purcell |
| 2014/0099379 | A1 | 4/2014 | Beck-Broichsitter et al. |
| 2014/0249235 | A1 | 9/2014 | Brugel et al. |
| 2014/0302154 | A1 | 10/2014 | Waldoefner et al. |
| 2014/0356443 | A1 | 12/2014 | Brisander et al. |
| 2015/0218198 | A1 | 8/2015 | Petermann et al. |
| 2015/0290233 | A1* | 10/2015 | Yarden ............... A61K 31/7032 |
| | | | 514/33 |
| 2015/0298084 | A1 | 10/2015 | Schoeppe et al. |
| 2015/0342923 | A1 | 12/2015 | Powell |
| 2016/0051484 | A1 | 2/2016 | Kataoka et al. |
| 2016/0235677 | A1 | 8/2016 | Hoerr et al. |
| 2016/0317459 | A1 | 11/2016 | Ensign et al. |
| 2016/0346266 | A1 | 12/2016 | Tolleth et al. |
| 2017/0042823 | A1 | 2/2017 | Prud'homme et al. |
| 2017/0209386 | A1 | 7/2017 | Pagels et al. |
| 2018/0125915 | A1 | 5/2018 | Mikhail |
| 2019/0008788 | A1 | 1/2019 | Prud'homme et al. |
| 2019/0105293 | A1* | 4/2019 | Howes .................. A61K 9/145 |
| 2019/0151252 | A1 | 5/2019 | Pagels et al. |
| 2019/0192444 | A1 | 6/2019 | Barzilay et al. |
| 2020/0023332 | A1 | 1/2020 | Prud'homme et al. |
| 2020/0147032 | A1* | 5/2020 | Prud'Homme ...... A61K 9/0095 |
| 2020/0206136 | A1 | 7/2020 | Prud'homme et al. |
| 2020/0215027 | A1 | 7/2020 | Prud'homme et al. |
| 2022/0062223 | A1 | 3/2022 | Prud'homme et al. |
| 2023/0172949 | A1 | 6/2023 | Brough et al. |
| 2023/0210812 | A1 | 7/2023 | Prud'homme et al. |
| 2023/0285352 | A1 | 9/2023 | Prud'homme et al. |
| 2024/0261254 | A1 | 8/2024 | Prud'homme et al. |
| 2024/0408050 | A1 | 12/2024 | Prud'homme et al. |

FOREIGN PATENT DOCUMENTS

| | | | |
|---|---|---|---|
| CN | 100389766 C | 5/2008 | |
| CN | 102048160 A | 5/2011 | |
| CN | 102058560 A | 5/2011 | |
| CN | 102334609 A | 2/2012 | |
| CN | 104042567 A | 9/2014 | |
| CN | 104666293 A | 6/2015 | |
| CN | 105213250 A | 1/2016 | |
| CN | 105796512 A | 7/2016 | |
| CN | 106750272 A | 5/2017 | |
| CN | 107334729 A * | 11/2017 | ......... A61K 31/7032 |
| CN | 107536830 A | 1/2018 | |
| CN | 108524493 A | 9/2018 | |
| EP | 4008314 A2 | 6/2022 | |
| JP | 2015-129128 | 7/2015 | |
| WO | 1994008599 A1 | 4/1994 | |
| WO | WO 1994/008610 A1 | 4/1994 | |
| WO | 1997049736 A2 | 12/1997 | |
| WO | WO 1999/056727 A2 | 11/1999 | |
| WO | 2002076441 A1 | 10/2002 | |
| WO | 2002078674 A1 | 10/2002 | |
| WO | WO 2002/092069 A1 | 11/2002 | |
| WO | WO 2009/067734 A1 | 6/2009 | |
| WO | 2009080164 A1 | 7/2009 | |
| WO | 2013023003 A1 | 2/2013 | |
| WO | WO 2014/140991 A1 | 9/2014 | |
| WO | 2015130835 A1 | 9/2015 | |
| WO | WO 2015/140138 A1 | 9/2015 | |
| WO | 2015200054 A2 | 12/2015 | |
| WO | 2015200054 A9 | 12/2015 | |
| WO | 2016193810 A1 | 12/2016 | |
| WO | 2017089942 | 6/2017 | |
| WO | 2017112828 A1 | 6/2017 | |
| WO | WO 2017/130046 A1 | 8/2017 | |
| WO | 2019055539 A1 | 3/2019 | |
| WO | WO 2019/050969 A1 | 3/2019 | |
| WO | 2019090030 A1 | 5/2019 | |
| WO | 2020018890 A1 | 1/2020 | |
| WO | WO 2020/099937 A2 | 5/2020 | |

(56) References Cited

FOREIGN PATENT DOCUMENTS

| WO | 2020227350 A1 | 11/2020 |
| WO | 2020252346 A1 | 12/2020 |
| WO | 2021046078 A1 | 3/2021 |

OTHER PUBLICATIONS

C Wang et al., Enhancing Bioavailability of Dihydromyricetin through Inhibiting Precipitation of Soluble Cocrystals by a Crystallization Inhibitor, 2016, Cryst. Frowth Des., 16(9), 5030-5039, DOI: 10.1021/acs.cgd.6b00591 (Year: 2016).*

PubChem "Dihydromyricetin" (https://pubchem.ncbi.nlm.nih.gov/compound/161557; accessed Jun. 1, 2023) (Year: 2023).*

Cech et al. (https://www.pharmaexcipients.com/wp-content/uploads/2020/07/7.-Kollicoat-SR-30-D-483-Combination-with-MAE.pdf; accessed Jun. 1, 2023; presented Apr. 2016) (Year: 2016).*

Cuomo et al., Carbonated beverages and gastrointestinal system: Between myth and reality, 2009, Nutrition, Metabolism and Cardiovascular Diseases, 19(1), 683-689, DOI: 10.1016/j.numecd.2009.03.020 (Year: 2009).*

Shen et al., Dihydromyricetin as a Novel Anti-Alcohol Intoxication Medication, 2012, J Neurosci, 32(1), 390-401, DOI: 10.1523/JNEUROSCI.4639-11.2012 (Year: 2012).*

Baek et al., Antioxidant Properties of a Dihydromyricetin-Rich Extract from Vine Tea (*Ampelopsis grossedentata*) in Menhaden Oil, 2015, Research & Reviews: Journal of Botanical Sciences, 4(3), 53-63, e-ISSN:2320-0189 (Year: 2015).*

Liu et al., Characterization and antioxidant activity of dihydromyricetin-lecithin complex, 2009, Eur Food Res Technol, 230, 325-331, DOI: 10.1007/s00217-009-1175-0 (Year: 2009).*

Liu et al., Characterization, Stability and Antioxidant Activity of the Inclusion Complex of Dihydromyricetin With Hydroxypropyl-b-Cyclodextrin, 2012, Journal of Food Biochemistry, 36, 634-641, DOI: 0.1111/j.1745-4514.2011.00577.x (Year: 2011).*

Liang et al., Dihydromyricetin Ameliorates Behavioral Deficits and Reverses Neuropathology of Transgenic Mouse Models of Alzheimer's Disease, 2014, Neurochem Res, 39, 1171-1181, DOI: 10.1007/s11064-014-1304-4 (Year: 2014).*

JT Wang et al., Protective Effect of Dihydromyricetin Against Lipopolysaccharide-Induced Acute Kidney Injury in a Rat Model, 2016, Med Sci Monit, 22, 454-459, DOI: 10.12659/MSM.897076 (Year: 2016).*

Morales et al., Hovenia dulcis Thunb. pseudofruits as functional foods: Phytochemicals and bioactive properties in different maturity stages, 2017, Journal of Functional Foods, 29, 37-45, DOI: 10.1016/j.jff.2016.12.003 (Year: 2017).*

Yu et al., Evidence-based prevention of Alzheimer's disease: systematic review and meta-analysis of 243 observational prospective studies and 153 randomised controlled trials, 2020, J Neural Neurosurg Psychiatry, 91, 1201-1209, DOI: 10.1136/jnnp-2019-321913 (Year: 2020).*

Loomans-Kropp et al., Cancer prevention and screening: the next step in the era of precision medicine, 2019, NJP Precision Onc., 3(3), 75-79, DOI: 10.1038/s41698-018-0075-9 (Year: 2019).*

Naveed et al., Pharmacological Primary Prevention of Diabetes Mellitus Type II: A Narrative Review, 2020, Cureus, 12(8), 1-10, DOI: 10.7759/cureus.10033 (Year: 2020).*

Lundberg. https://www.medscape.com/viewarticle/885865?form=fpf. Published: 2017.*

CN107334729 Eng Tran. Published: Nov. 10, 2017.*

Ren. Acta Pharmacologica Sinica (2016) 37: 1315-1324.*

CN100389766 Eng Tran. Published: May 28, 2008.*

Aungst, B.J., "Absorption Enhancers: Applications and Advances", AAPS J., (2012) vol. 14, No. 1, pp. 10-18.

Anton, N. et al., "Nano-emulsions and nanocapsules by the PIT method: an investigation on the role of the temperature cycling on the emulsion phase inversion", Int'l J. Pharmaceutics, (2007) vol. 344, Nos. 1-2, pp. 44-52.

Anton, N. & Vandamme, T.F., "The universality of low-energy nano-emulsification", Int'l J. Pharmaceutics, (2009) vol. 377, Nos. 1-2, pp. 142-147.

Babu, N.J. & Nangia, A., "Solubility Advantage of Amorphous Drugs and Pharmaceutical Cocrystals", Crystal Growth & Design, (2011) vol. 11, pp. 2662-2679.

Bailly, N. et al. "Poly(N-vinylpyrrolidone)-block-poly(vinyl acetate) as a Drug Delivery Vehicle for Hydrophobic Drugs", Biomacromolecules, (2012) vol. 13, pp. 4109-4117.

BASF, Luviscol VA Grades Technical Information, Jun. 2012, pp. 1-14.

Bouchemal, K. et al., "Nano-emulsion formulation using spontaneous emulsification: solvent, oil and surfactant optimization", Int'l J. Pharmaceutics, (2004) vol. 280, Nos. 1-2, pp. 241-251.

Breitenbach, J., "Melt extrusion: from process to drug delivery technology", European J. Pharmaceutics & Biopharmaceutics, (2002) vol. 54, No. 2, pp. 107-117.

Chokshi, R. & Zia, H., "Hot-Melt Extrusion Technique: A Review", Iranian J. Pharmaceutical Research, (2004) vol. 3, pp. 3-16.

"The Complete Guide to Enteric Coating", https://astenzymes.com/the-complete-guide-to-enteric-coating/, accessed Aug. 11, 2020, pp. 1-11.

Crowley, M.M., et al., "Pharmaceutical applications of hot-melt extrusion: part I", Drug Development & Industrial Pharmacy, (2007) vol. 33, No. 9, pp. 909-926.

D'Addio, S.M. & Prud'Homme, R.K., "Controlling drug nanoparticle formation by rapid precipitation", Advanced Drug Delivery Reviews, (2011) vol. 63, No. 6, pp. 417-426.

Davies, D.L. et al., "Recent Advances in the Discovery and Preclinical Testing of Novel Compounds for the Prevention and/or Treatment of Alcohol Use Disorders", Alcoholism: Clinical & Experimental Research, (2013) vol. 37, No. 1, pp. 8-15.

"Enteric Coating—The Enteric Coating Process", https://www.xtend-life.com/pages/enteric-coating, accessed Aug. 12, 2020, pp. 1-6.

Etchenausia, L. et al., "RAFT/MADIX emulsion copolymerization of vinyl acetate and N-vinylcaprolactam: towards waterborne physically crosslinked thermoresponsive particles", Polymer Chemistry, (2017) DOI: 10.1039/C7PY00221A, pp. 1-28.

Fang, H.-L. et al., "Treatment of Chronic Liver Injuries in Mice by Oral Administration of Ethanolic Extract of the Fruit of Hovenia dulcis", American J. of Chinese Medicine, (2007), vol. 35, No. 4, pp. 693-703.

Ganachaud, F. & Katz, J.L., "Nanoparticles and Nanocapsules Created Using the Ouzo Effect: Spontaneous Emulsification as an Alternative to Ultrasonic and High-Shear Devices", ChemPhysChem, (2005) vol. 6, No. 2, pp. 209-216.

Guo, Q. et al., "Binding of dihydromyricetin and its metal ion complexes with bovine serum albumin", Biotechnology & Biotechnological Equipment, (2014) vol. 28, No. 2, pp. 333-341.

Guo, Q. et al., "Biosynthesis of gold nanoparticles using a kind of flavanol: Dihydromyricetin", Colloids & Surfaces A: Physicochem. & Engineering Aspects, (2014) vol. 441, pp. 127-132.

Guo, Q. et al., "Synthesis of dihydromyricetin-manganese (II) complex and interaction with DNA", J. Molecular Structure, (2012) vol. 1027, pp. 64-69.

Gupta, A. et al., "Nanoemulsions: formation, properties and applications", Soft Matter, (2016) vol. 12, No. 11, pp. 2826-2841.

Hase, K. et al., "Hepatoprotective Effect of Hovenia dulcis THUNB. on Experimental Liver Injuries Induced by Carbon Tetrachloride or D-Galactosamine/Lipopolysaccharide", Biol. Pharm. Bull., (1997) vol. 20, No. 4, pp. 381-385.

Hu, J. et al., "Nanoparticle Engineering Processes for Enhancing the Dissolution Rates of Poorly Water Soluble Drugs", Drug Development & Industrial Pharmacy, (2004) vol. 30, No. 3, pp. 233-245.

International Patent Application PCT/US2018/049580 International Search Report dated Jan. 15, 2019.

International Patent Application PCT/US2018/049580 Written Opinion dated Jan. 15, 2019.

International Patent Application PCT/IB2019/001381 International Search Report dated Jun. 23, 2020.

International Patent Application PCT/IB2019/001381 Written Opinion dated Jun. 23, 2020.

(56) References Cited

OTHER PUBLICATIONS

International Patent Application PCT/US2020/037542 International Search Report dated Sep. 11, 2020.

International Patent Application PCT/US2020/037542 Written Opinion dated Sep. 11, 2020.

Izquierdo, P. et al., "Formation and Stability of Nano-Emulsions Prepared Using the Phase Inversion Temperature Method", Langmuir, (2002) vol. 18, No. 1, pp. 26-30.

Jain, M.S. et al., "Spray Drying in Pharmaceutical Industry: A Review", Research J. Pharma. Dosage Forms & Tech., (2011), vol. 4, No. 2, pp. 74-79.

Kelmann, R.G. et al., "Carbamazepine parenteral nanoemulsions prepared by spontaneous emulsification process", Int'l J. Pharmaceutics, (2007) vol. 342, Nos. 1-2, pp. 231-239.

Li, H. et al., "The Versatile Effects of Dihydromyricetin in Health", Evidence Based Complementary & Alternative Medicine, (2017) Art. ID 1053617, pp. 1-10.

Liang, J. & Olsen, R.W., "Alcohol use disorders and current pharmacological therapies: the role of GABAA receptors", Acta Pharmacologica Sinica, (2014) vol. 35, No. 8, pp. 981-993.

Liang, J., et al., "Dihydromyricetin Prevents Fetal Alcohol Exposure-Induced Behavioral and Physiological Deficits: The Roles of GABAA Receptors in Adolescence", Neurochemical Research, (2014) vol. 39, No. 6, pp. 1147-1161.

Liu, Y. et al., "Mixing in a multi-inlet vortex mixer (MIVM) for flash nano-precipitation", Chemical Engineering Science, (2008), vol. 63, No. 11, pp. 2829-2842.

Maniruzzaman, M. et al., "A Review of Hot-Melt Extrusion: Process Technology to Pharmaceutical Products", ISRN Pharmaceutics, (2012) vol. 2012, Article ID 436763, pp. 1-9.

Murakami, H. et al., "Preparation of poly (DL-lactide-co-glycolide) nanoparticles by modified spontaneous emulsification solvent diffusion method", Int'l J. Pharmaceutics, (1999) vol. 187, No. 2, pp. 143-152.

Niwa, T. et al., "Preparations of biodegradable nanospheres of water-soluble and insoluble drugs with D,L-lactide/glycolide copolymer by a novel spontaneous emulsification solvent diffusion method, and the drug release behavior", J. Controlled Release, (1993) vol. 25, Nos. 1-2, pp. 89-98.

Okuma, Y. et al., "Effect of Extracts from Hovenia dulcis Thunb. on Alcohol Concentration in Rats and Men Administered Alcohol", J. Japan Society of Nutrition & Food Sciences, (1995), vol. 48, No. 3, pp. 167-172 (English-language abstract).

Onoue, S. et al., "Self-micellizing solid dispersion of cyclosporine A with improved dissolution and oral bioavailability", Eur. J. Pharm. Sci., (2014), vol. 62, pp. 16-22.

Patil, H. et al., "Hot-Melt Extrusion: from Theory to Application in Pharmaceutical Formulation", AAPS PharmSciTech, (2016) vol. 17, No. 1, pp. 20-42.

Prudic, A. et al., "Influence of Copolymer Composition on the Phase Behavior of Solid Dispersions", Molecular Pharmaceutics, (2014) vol. 11, pp. 4189-4198.

Rang, M.-J. & Miller, C.A., "Spontaneous Emulsification of Oils Containing Hydrocarbon, Nonionic Surfactant, and Oleyl Alcohol", J. Colloid & Interface Science, (1999) vol. 209, No. 1, pp. 179-192.

Roger, K. et al., "Formation of 10—100 nm Size-Controlled Emulsions through a Sub-PIT Cycle", Langmuir, (2010) vol. 26, No. 6, pp. 3860-3867.

Roger, K. et al., "Emulsification through Surfactant Hydration: The PIC Process Revisited", Langmuir, (2011) vol. 27, No. 2, pp. 604-611.

Roger, K. et al., "Superswollen Microemulsions Stabilized by Shear and Trapped by a Temperature Quench", Langmuir, (2011) vol. 27, No. 17, pp. 10447-10454.

Ruan, L.-P. et al., "Improving the solubility of ampelopsin by solid dispersions and inclusion complexes", J. Pharmaceutical & Biomedical Analysis, (2005) vol. 38, pp. 457-464.

Ruschak, K.J. & Miller, C.A., "Spontaneous Emulsification in Ternary Systems with Mass Transfer", Industrial & Engineering Chemistry Fundamentals, (1972) vol. 11, No. 4, pp. 534-540.

Saad, W.S. & Prud'Homme, R.K., "Principles of nanoparticle formation by flash nanoprecipitation", Nano Today, (2016) vol. 11, No. 2, pp. 212-227.

Saberi, A.H. et al., "Fabrication of vitamin E-enriched nanoemulsions: Factors affecting particle size using spontaneous emulsification", J. Colloid & Interface Science, (2013), vol. 391, pp. 95-102.

Sacks, J.J. et al., "2010 National and State Costs of Excessive Alcohol Consumption", American J. of Preventive Medicine, (2015), vol. 49, No. 5, pp. e73-e79.

Savjani, K.T. et al., "Drug solubility: importance and enhancement techniques", ISRN Pharmaceutics, (2012), vol. 2012, Article ID 195727, pp. 1-10.

Sheela, D.L. et al., "Lauric acid induce cell death in colon cancer cells mediated by the epidermal growth factor receptor downregulation: An in silico and in vitro study", Human & Experimental Toxicology, (Epub. Apr. 3, 2019) DOI: 10.1177/0960327119839185, pp. 1-9.

Solanki, S.S. et al., "Microemulsion Drug Delivery System: For Bioavailability Enhancement of Ampelopsin", International Scholarly Research Network, ISRN Pharmaceutics, (2012) vol. 2012, Article ID 108164, pp. 1-4.

Solans, C. et al., "Nano-emulsions", Current Opinion in Colloid & Interface Science, (2005) vol. 10, Nos. 3-4, pp. 102-110.

Taisne, L. & Cabane, B., "Emulsification and Ripening following a Temperature Quench", Langmuir, (1998) vol. 14, No. 17, pp. 4744-4752.

Tang, C. et al., "Polymer Directed Self-Assembly of pH-Responsive Antioxidant Nanoparticles", Langmuir, (2015), vol. 31, No. 12, pp. 3612-3620.

Thanou, M. et al., Oral drug absorption enhancement by chitosan and its derivatives, Advanced Drug Delivery Reviews, (2001) vol. 52, No. 2, pp. 117-126.

Tong, Q. et al., "Determination of dihydromyricetin in rat plasma by LC-MS/MS and its application to a pharmacokinetic study", J. Pharmaceutical & Biomedical Analysis, (2015) vol. 114, pp. 455-461.

U.S. Appl. No. 16/683,387 Requirement for Restriction/Election dated Dec. 3, 2020.

U.S. Appl. No. 16/683,387 Office Action dated Jul. 14, 2021.

U.S. Appl. No. 16/683,387 Office Action dated Apr. 13, 2022.

U.S. Appl. No. 16/810,710 Requirement for Restriction/Election dated Jan. 6, 2021.

U.S. Appl. No. 16/810,710 Office Action dated May 12, 2021.

U.S. Appl. No. 16/810,710 Office Action dated Mar. 30, 2022.

U.S. Appl. No. 16/723,127 Requirement for Restriction/Election dated Jun. 1, 2021.

U.S. Appl. No. 16/723,127 Office Action dated Sep. 15, 2021.

U.S. Appl. No. 17/320,945 Office Action dated Apr. 26, 2023.

U.S. Appl. No. 17/320,945 Office Action dated Sep. 19, 2023.

U.S. Appl. No. 17/694,571 Requirement for Restriction/Election dated Jul. 20, 2023.

U.S. Appl. No. 17/694,571 Office Action dated Dec. 20, 2023.

U.S. Appl. No. 17/899,157 Requirement for Restriction/Election dated Oct. 30, 2023.

U.S. Appl. No. 17/943,691 Requirement for Restriction/Election dated Aug. 16, 2023.

Wang, C. et al., "Enhancing bioavailability of dihydromyricetin through inhibiting precipitation of soluble cocrystals by a crystallization inhibitor", Crystal Growth & Design, (2016) vol. 16, No. 9, pp. 5030-5039.

Weissmueller, N.T. et al., "Nanocarriers from GRAS zein proteins to encapsulate hydrophobic actives", Biomacromolecules, (2016), vol. 17, No. 11, pp. 3828-3837.

Whitehead, K. & Mitragotri, S., "Mechanistic Analysis of Chemical Permeation Enhancers for Oral Drug Delivery", Pharmaceutical Research, (2008), vol. 25, No. 6, pp. 1412-1419.

Whitehead, K. et al., "Safe and Effective Permeation Enhancers for Oral Drug Delivery", Pharmaceutical Research, (2008) vol. 25, No. 8, pp. 1782-1788.

Yao, M.-J. & Huang, J.-H., "Study on the Microencapsulation of Dihydromyricetin", J. Jishou University (Natural Science Edition), (2007) vol. 28, No. 3, pp. 107-111 (English-language abstract).

(56) References Cited

OTHER PUBLICATIONS

Zhang, J. et al., "Recent Update on the Pharmacological Effects and Mechanisms of Dihydromyricetin", Frontiers in Pharmacol., (Oct. 25, 2018) vol. 9, article 1204, pp. 1-11, https://doi.org/10.3389/fphar.2018.01204.

Zhang, X. et al., "Evaluation and manipulation of the key emulsification factors toward highly stable PCM-water nano-emulsions for thermal energy storage", Solar Energy Materials & Solar Cells, (2021) vol. 219, No. 110820, pp. 1-11.

Zhang, X.-Y. et al., "Scavenging Effect of Dihydromyricetin on the Free Radicals by ESR", Modern Food Science & Technology, (2010) vol. 26, issue 10, pp. 1040-1042, 1070 (English-language abstract).

Zhang, Y. et al., "Design and Solidification of Fast-Releasing Clofazimine Nanoparticles for Treatment of Cryptosporidiosis", Molecular Pharmaceutics, (2017) vol. 14, No. 10, pp. 3480-3488.

Ji, Y. et al., "Effects of Fruits of Hovenia dulcis Thunb on Acute Alcohol Toxicity in Mice", J. Chinese Medicinal Materials, (2001) vol. 24, issue 2, pp. 126-128 (English-language abstract).

Ji, Y. et al., "Effects of Hovenia dulcis Thunb on Blood Sugar and Hepatic Glycogen in Diabetic Mice", J. Chinese Medicinal Materials, (2002) vol. 25, issue 3, pp. 190-191 (English-language abstract).

Fernandez, P. et al., "Nano-emulsion formation by emulsion phase inversion", Colloids & Surfaces A: Physicochem. Eng. Aspects, (2004) vol. 251, Nos. 1-3, pp. 53-58.

U.S. Appl. No. 17/899,157 Office Action dated Aug. 6, 2025.

U.S. Appl. No. 17/943,691 Notice of Allowance and Notice of Allowability dated Feb. 27, 2025.

U.S. Appl. No. 18/641,369 Office Action dated Aug. 12, 2025.

U.S. Appl. No. 18/641,369 Requirement for Restriction/Election dated Feb. 26, 2025.

Antonov et al., "Entering and Exiting the Protein—Polyelectrolyte Coacervate Phase via Nonmonotonic Salt Dependence of Critical Conditions", Biomacromolecules, vol. 11, No. 1, pp. 51-59 (2010).

Bilati et al., "Development of a nanoprecipitation method intended for the entrapment of hydrophilic drugs into nanoparticles", European J. Pharmaceutical Sciences, vol. 24, pp. 67-75 (2005).

Bilati et al., "Nanoprecipitation Versus Emulsion-based Techniques for the Encapsulation of Proteins Into Biodegradable Nanoparticles and Process-related Stability Issues", AAPS PharmSciTech, vol. 6, No. 4, Article 74, pp. E594-E604 (2005).

Choi et al., "Hydrophobic ion pair formation between leuprolide and sodium oleate for sustained release from biodegradable polymeric microspheres", International Journal of Pharmaceutics, vol. 203, pp. 193-202 (2000).

Crater et al., "Barrier Properties of Gastrointestinal Mucus to Nanoparticle Transport," Macromolecular Bioscience, vol. 10, No. 12, pp. 1473-1483 (2010).

Cu et al., "Drug delivery: Stealth particles give mucus the slip", Nature Materials, vol. 8, No. 1, pp. 11-13 (Jan. 2009).

Davies et al., "Recent advances in the management of cystic fibrosis", Archives of Disease in Childhood, vol. 99, No. 11, pp. 1033-1036 (2014).

De Azevedo et al., "Mastoparan induces apoptosis in B16F10-Nex2 melanoma cells via the intrinsic mitochondrial pathway and displays antitumor activity in vivo", Peptides, vol. 68, pp. 113-119 (2015).

Deng et al., "Janus Nanoparticles of Block Copolymers by Emulsion Solvent Evaporation Induced Assembly", Macromolecules, vol. 49, pp. 1362-1368 (2016).

Ensign et al., "Oral drug delivery with polymeric nanoparticles: The gastrointestinal mucus barriers," Advanced Drug Delivery Reviews, vol. 64, No. 6, pp. 557-570 (2012).

Extended European Search Report (EESR) dated Jan. 8, 2018 in European Application No. 15811879.4.

Galindo-Rodriguez et al., "Polymeric Nanoparticles for Oral Delivery of Drugs and Vaccines: A Critical Evaluation of In Vivo Studies", Critical Reviews in Therapeutic Drug Carrier Systems, vol. 22, No. 5, pp. 419-463 (2005).

Gessner et al., "Nanoparticles Modified with Cell-Penetrating Peptides: Conjugation Mechanisms, Physicochemical Properties, and Application in Cancer Diagnosis and Therapy", International Journal of Molecular Sciences, vol. 21, 2536, pp. 1-21 (2020).

Hoiby, "Recent advances in the treatment of Pseudomonas aeruginosa infections in cystic fibrosis", BMC Medicine, vol. 9, No. 32, pp. 1-7 (2011).

Holland et al., "Polymers for Biodegradable Medical Devices, 1. The Potential of Polyesters as Controlled by Macromolecular Release Systems", Journal of Controlled Release, vol. 4, pp. 155-180 (1986).

Johnson et al., "Chemical Processing and Micromixing in Confined Impinging Jets", AIChE Journal, vol. 49, No. 9, pp. 2264-2282 (2003).

Johnson et al., "Engineering the Direct Precipitation of Stabilized Organic and Block Copolymer Nonparticles as Unique Composites", Abstracts of Papers of the American Chemical Society, No. 441 (Abstract) (Sep. 2003).

Johnson et al., "Flash NanoPrecipitation of Organic Actives and Block Copolymers using a Confined Impinging Jets Mixer," Australian Journal of Chemistry, vol. 56, No. 10, pp. 1021-1024 (2003).

Johnson et al., "Nanoprecipitation of Organic Actives Using Mixing and Block Copolymer Stabilization", Abstracts of Papers of the American Chemical Society, No. 186 (Abstract) (Sep. 2003).

Kader A. et al., "In Vitro Release of Theophylline from Poly(Lactic Acid) Sustained-Release Pellets. Prepared by Direct Compression.", Drug Development and Industrial Pharmacy, 24(6), 527-534 (1998).

Khanvilkar et al., "Drug transfer through mucus," Advanced Drug Delivery Reviews, vol. 48, Nos. 2-3, pp. 173-193 (2001).

Lai et al., "Mucus-penetrating nanoparticles for drug and gene delivery to mucosal tissues," Advanced Drug Delivery Reviews, vol. 61, No. 2, pp. 158-171 (2009).

Lai et al., "Rapid transport of large polymeric nanoparticles in fresh undiluted human mucus," Proceedings National Academy of Sciences, vol. 104, No. 5, pp. 1482-1487 (Jan. 30, 2007).

Lan et al. Preparation and Characterization of Super Cross-Linked Poly(ethylene oxide) Gel Polymer Electrolyte for Lithium-Ion Battery. Science of Advanced Materials, vol. 9, No. 6, Jun. 2017, pp. 988-994(7).

Liu et al., CFD Predictions for Chemical Processing in a Confined Impinging-Jets Reactor, AIChE Journal, vol. 52, No. 2, pp. 731-744 (Feb. 2006).

Livraghi et al., "Cystic Fibrosis and Other Respiratory Diseases of Impaired Mucus Clearance", Toxicologic Pathology, vol. 35, No. 1, pp. 116-129 (2007).

Mai et al., "Controlled Incorporation of Particles into the Central Portion of Vesicle Walls", J. Am. Chem. Soc., vol. 132, pp. 10078-10084 (2010).

Markwalter et al., "Inverse Flash NanoPrecipitation for Biologics Encapsulation: Understanding Process Losses via an Extraction Protocol", Control of Amphiphile Self-Assembling at the Molecular Level: Supra-Molecular Assemblies with Tuned Physicochemical Properties for Delivery Applications, pp. 275-296 (Jan. 1, 2017).

Muheem et al., "A review on the strategies for oral delivery of proteins and peptides and their clinical perspectives", Saudi Pharmaceutical Journal, vol. 24, No. 4, pp. 413-428 (2016).

Okuyama et al., "Preparation of functional nanostructured particles by spray drying", Advanced Powder Technol., vol. 17, No. 6, pp. 587-611 (2006).

Overbeek et al., "Phase separation in polyelectrolyte solutions. Theory of complex coacervation", Journal of Cellular Physiology, vol. 49, No. S1, pp. 7-26 (1957).

Pagels et al., "Inverse Flash NanoPrecipitation for Biologics Encapsulation: Nanoparticle Formation and Ionic Stabilization in Organic Solvents", ACS Publications, vol. 1271, pp. 249-27 4 (2017).

Pagels et al., "Polymeric nanoparticles and microparticles for the delivery of peptides, biologics, and soluble therapeutics", Journal of Controlled Release, vol. 219, pp. 519-535 & Supplemental Information (2015).

Pinkerton et al., "Formation of Stable Nanocarriers by in Situ Ion Pairing during Block-Copolymer-Directed Rapid Precipitation", Molecular Pharmaceutics, vol. 10, No. 1, pp. 319-328 (2013).

(56) References Cited

OTHER PUBLICATIONS

Pustulka et al., "Flash Nanoprecipitation: Particle Structure and Stability", Molecular Pharmaceutics, vol. 10, pp. 4367-4377 (2013).

Riess et al. "Emulsifying Properties of Block Copolymers. Oil-Water Emulsions and Microemulsions", Polym. Eng. Sci., vol. 17, No. 8, pp. 634-638 (1977).

Sahoo et al., "Characterization of Porous PLGA/PLA Microparticles as a Scaffold for Three Dimensional Growth of Breast Cancer Cells", Biomacromolecules, vol. 6, pp. 1132-1139 (2005).

Savjani, K.T. et al., "Drug Solubility: Importance and Enhancement Techniques", ISRN Pharmaceutics, vol. 2012, Article ID 195727, pp. 1-10 (2012).

Schwendeman et al., "Injectable controlled release depots for large molecules", Journal of Controlled Release, vol. 190, pp. 240-253 (37 pages) (Sep. 28, 2014).

Serajuddin, "Salt formation to improve drug solubility", Advanced Drug Delivery Reviews, vol. 59, No. 7, pp. 603-616 (2007).

Shah et al., Poly(glycolic acid-co-DL-lactic acid): diffusion or degradation controlled drug delivery?, Journal of Controlled Release, vol. 18, pp. 261-270 (1992).

Song et al., "A novel in situ hydrophobic ion pairing (HIP) formulation strategy for clinical product selection of a nanoparticle drug delivery system", Journal of Controlled Release, vol. 229, pp. 106-119 (2016).

The Dow Chemical Company, "Dow excipients for consumer health and pharmaceuticals", 3 pages, 2024, https://www.dow.com/en-us/document-viewer.html?randomVar=4113691100936629343&docPath=/content/dam/dcc/documents/118/118-01909-01-consumer-health-and-pharma-brochure.pdf, accessed Feb. 11, 2025.

U.S. Appl. No. 16/761,140 Notice of Allowance and Notice of Allowability dated Nov. 14, 2024.

U.S. Appl. No. 16/761,140 Examiner Initiated Interview Summary dated Nov. 14, 2024.

U.S. Appl. No. 17/320,945 Office Action dated Mar. 1, 2024.

U.S. Appl. No. 17/899,157 Office Action dated Oct. 23, 2024.

U.S. Appl. No. 17/899,157 Office Action dated Apr. 10, 2024.

U.S. Appl. No. 17/943,691 Office Action dated Jun. 18, 2024.

U.S. Appl. No. 17/943,691 Office Action dated Feb. 15, 2024.

Xu et al, "Scalable method to produce biodegradable nanoparticles that rapidly penetrate human mucus", Journal of Controlled Release, vol. 170, pp. 279-286 (2013).

Xu et al., "Influence of experimental parameters and the copolymer structure on the size control of nanospheres in double emulsion method", J. Polymer Research, vol. 18, pp. 131-137 (2011).

Ya-Chen, et al., Combined Tween 20-Stabilized Gold Nanoparticles and Reduced Graphite Oxide-Fe3O4 Nanoparticle Composites for Rapid and Efficient Removal of Mercury Species from a Complex Matrix, 2014, ACS Appl. Mater. Interfaces, 6, 17437-17445 (2014).

Zandonella, "Bob Prud'homme—Flash NanoPrecipitation" http://research.princeton.edu/news/features/a/index.xml?id=6234, accessed Mar. 9, 2018, originally published Dec. 9, 2011, pp. 1-2.

Zhou et al., "PEG -b-PCL polymeric nano-micelle inhibits vascular angiogenesis by activating p53-dependent apoptosis in zebrafish", International Journal of Nanomedicine, vol. 11, pp. 6517-6531 (2016).

Zhu et al., "Preparation and characterization of hCG-loaded polylactide or poly(lactide-co-glycolide) Microspheres using a modified water-in-oil-in-water (w/o/w) emulsion solvent evaporation technique", J. Microencapsulation, vol. 18, No. 2, pp. 247-260 (2001).

* cited by examiner

1

FORMULATIONS OF DIHYDROMYRICETIN AND A PERMEABILIZER

This application is a Section 371 U.S. National Stage of International Application No. PCT/US2020/037542, filed Jun. 12, 2020, which was published as International Application No. WO/2020/252346 on Dec. 17, 2020, which claims the benefit of U.S. Provisional Application No. 62/861,895, filed Jun. 14, 2019.

FIELD OF THE INVENTION

The invention pertains to compositions including dihydromyricetin (DHM) and a fatty acid or a fatty acid salt that can act as a permeabilizer.

BACKGROUND

Alcohol is a constituent of medicines, foods, and beverages that provides both beneficial and detrimental effects on human beings. Alcohol can refer to ethyl alcohol (ethanol), which is the common form of consumable alcohol found in alcoholic beverages, e.g., such as beer, wine, and liquor. During consumption, alcohol is rapidly absorbed from the stomach and small intestine into the bloodstream, from which it can affect several organs, including the brain, heart, pancreas, and liver. Alcohol can act as a depressant to the central nervous system (CNS). For example, alcohol interferes with the brain's communication pathways, which affects brain functionality that manifests in cognitive and behavioral changes, e.g., such as a person's ability to think, focus, and move, as well as his/her mood and behavior. Alcohol can cause inflammation of and damage to the liver; e.g., consistent heavy drinking can cause chronic liver problems. For example, heavy drinking can lead to steatosis (e.g., fatty liver), infection (e.g., alcoholic hepatitis), fibrosis, and cirrhosis. More commonly, even a single instance of light to moderate to heavy alcohol consumption can result in what is commonly known as an "alcohol hangover". A hangover refers to an array of physical symptoms that affect a person shortly after ingesting alcohol, e.g., within hours of consumption. The symptoms of a hangover include, for example, one or more of thirst, fatigue and/or weakness, headache and/or muscle aches, dizziness/faintness, loss of appetite, poor and/or decreased sleep, nausea and/or stomach pain (e.g., which can include vomiting), and elevated heart rate. A hangover is considered to be one of the most widely experienced negative consequences of consuming ethanol.[1]

SUMMARY OF THE INVENTION

An embodiment of the invention includes a dihydromyricetin (DHM) formulation that includes dihydromyricetin (DHM) and a permeabilizer including a fatty acid salt and/or a fatty acid. The permeabilizer can include a fatty acid salt, such as a sodium fatty acid salt, a potassium fatty acid salt, a saturated fatty acid salt, a sodium saturated fatty acid salt, a potassium saturated fatty acid salt, a sodium saturated fatty acid salt and/or a potassium saturated fatty acid salt having 4, 5, 6, 7, 8, 9, 10, 11, 12, 13, 14, 15, 16, 17, 18, 19, or 20 carbons, sodium decanoate (sodium caprate), and/or potassium decanoate (potassium caprate). The permeabilizer can include a fatty acid, such as a saturated fatty acid, a saturated fatty acid having 4, 5, 6, 7, 8, 9, 10, 11, 12, 13, 14, 15, 16, 17, 18, 19, or 20 carbons, a saturated fatty acid having 7, 8, 9, 10, 11, 12, or 13 carbons, and/or decanoic acid (capric acid). The fatty acid can be in the form of a triglyceride; for example, the fatty acid can be decanoic acid (capric acid) bonded to glycerol in a medium chain triglyceride or the fatty acid can be decanoic acid (capric acid) in a medium chain triglyceride formed of three decanoic acid (capric acid) groups bonded to glycerol.

The DHM formulation can include a medium chain triglyceride formulation. The medium chain triglyceride formulation can include the fatty acid, and the fatty acid can include decanoic acid (capric acid). The DHM formulation can include coconut oil. The coconut oil can include the fatty acid, and the fatty acid can include decanoic acid (capric acid). The DHM formulation can include coconut product, palm kernel oil, palm oil, and/or durian extract. The coconut product, palm kernel oil, palm oil, and/or durian extract can include the fatty acid, and the fatty acid can include decanoic acid (capric acid). A fatty acid, decanoic acid (capric acid), a triglyceride, and/or a medium chain triglyceride can be a component of a natural product; the DHM formulation can include that natural product.

The DHM formulation can include at least 1, at least 2, at least 3, at least 4, or at least 5 mass units of permeabilizer per mass unit of DHM. The DHM formulation can include from about 1 to about 2 or from about 1 to about 3 mass units of permeabilizer per mass unit of DHM.

The DHM can be in solid form and/or powder form. The DHM can be crystalline; for example, the DHM can be at least 99%, at least 98%, at least 95%, at least 90%, at least 80%, at least 70%, at least 60%, or at least 50% crystalline. The DHM can be substantially amorphous or amorphous. The DHM can be solubilized, emulsified, dispersed as a suspension, dispersed as a colloid, or molecularly dispersed.

The DHM formulation can be homogeneous.

An embodiment of the invention includes a dosage form that includes the DHM formulation as a tablet, caplet, pill, pastille, troche, or lozenge.

An embodiment of the invention includes a dosage form that encapsulates the DHM formulation in a capsule. The capsule can be a soft gel capsule. For example, the dihydromyricetin (DHM) formulation can be in a liquid or gel form and can be encapsulated in a soft gel capsule. The capsule can include animal-derived material, such as gelatin and/or collagen, can include plant-derived material, and can include synthetically-produced material. For example, the capsule can include a polysaccharide, a sulfated polysaccharide, a carrageenan, cellulose, a cellulose derivative, starch, a starch derivative, pullulan, polyvinyl alcohol (PVA), polyvinyl alcohol (PVA) copolymer, and/or polyethylene glycol (PEG). For example, the capsule can include hydroxypropyl methylcellulose (HPMC) and/or hydroxypropyl methyl cellulose acetate succinate (HPMCAS). For example, the capsule can include material of algal origin and/or material derived from material of algal origin.

The dosage form can include an exterior surface, and the exterior surface can be coated with an enteric coating. For example, the exterior surface of the capsule, tablet, caplet, pill, pastille, troche, or lozenge can be coated with an enteric coating. The enteric coating can be a polymeric coating, a methacrylate copolymer coating, or a poly(methacrylic acid-co-ethyl acrylate) coating.

The dosage form can be not solubilized or dissolved by an aqueous solution having a pH of at most 3.5 (the dosage form can remain not solubilized or dissolved in an aqueous solution having a pH of 3.5 or less). The dosage form can be not solubilized or dissolved by an aqueous solution having a pH of at most 2 (the dosage form can remain not solubilized or dissolved in an aqueous solution having a pH of 2 or less).

The dosage form can be solubilized or dissolved by water or an aqueous solution having a pH of at least 5.5 (the dosage form can solubilize or dissolve in water or an aqueous solution having a pH of 5.5 or more). The dosage form can be solubilized or dissolved by water or an aqueous solution having a pH of at least 7 (the dosage form can solubilize or dissolve in water or an aqueous solution having a pH of 7 or more).

A dosage form can include the DHM formulation in a liquid or gel form.

A dosage form can include the dihydromyricetin (DHM) formulation with the DHM dissolved, emulsified, dispersed as a suspension, or dispersed as a colloid in an aqueous liquid. For example, particles including DHM that are of a size from 1 to 1000 nm can be considered to form a colloid in an aqueous liquid. For example, particles including DHM that are of a size greater than 1000 nm can be considered to form a suspension in an aqueous liquid. The aqueous liquid can include at least 0.04 wt % DHM, at least 0.07 wt % DHM, at least 0.1 wt % DHM, at least 0.14 wt % DHM, at least 0.2 wt % DHM, at least 0.4 wt % DHM, at least 1 wt % DHM, at least 2 wt % DHM, at least 3 wt % DHM, at least 4 wt % DHM, at least 5 wt % DHM, at least 6 wt % DHM, at least 7 wt % DHM, or at least 8 wt % DHM. The aqueous liquid can include cysteine; for example, the aqueous liquid can include at least 0.02 wt % cysteine, at least 0.05 wt % cysteine, at least 0.1 wt % cysteine, at least 0.2 wt % cysteine, at least 0.3 wt % cysteine, at least 0.4 wt % cysteine, at least 0.5 wt % cysteine, or at least 1 wt % cysteine. The aqueous liquid can include an emulsifier, such as a plant product, lecithin, or another emulsifier. The aqueous liquid can include carbon dioxide; for example, the aqueous liquid can include at least 0.1 wt % carbon dioxide, at least 0.2 wt % carbon dioxide, at least 0.3 wt % carbon dioxide, at least 0.4 wt % carbon dioxide, at least 0.5 wt % carbon dioxide, at least 0.8 wt % carbon dioxide, or at least 1.5 wt % carbon dioxide. The aqueous liquid can have a pH of at most 7 (a pH of 7 or less), at most 6 (a pH of 6 or less), at most 5 (a pH of 5 or less), or at most 4 (a pH of 4 or less). The aqueous liquid can include a water-soluble polymer, for example, poly(vinylpyrrolidone) (PVP), poly(vinylpyrrolidone-co-vinyl acetate) (PVP-VA), a cellulosic polymer, hydroxypropyl methylcellulose (HPMC), hydroxypropyl methylcellulose acetate succinate (HPMCAS), and/or carboxymethyl cellulose (CMC). The aqueous liquid can include a cyclodextrin, for example, beta-cyclodextrin.

The dosage form can further include a matrix material, such as poly(ethylene oxide), a cellulosic polymer, hydroxypropyl methylcellulose (HPMC), hydroxypropyl methylcellulose acetate succinate (HPMCAS), poly(vinylpyrrolidone-co-vinyl acetate) (PVP-VA), and/or poly(vinyl acetate-co-vinyl caprolactam-co-ethylene oxide) (such as Soluplus®). The DHM and/or the permeabilizer can be molecularly dispersed in the matrix material. The DHM can be amorphous in the matrix material.

The dihydromyricetin (DHM) formulation can be for use as a medicament. For example, the dihydromyricetin (DHM) formulation can be for use in reducing hangover symptoms, for use in preventing an alcohol use disorder, for use in preventing alcoholism, for use in treating an alcohol use disorder, for use in treating alcoholism, for use in treating an alcohol overdose, for use in increasing antioxidant capacity, for use in neuroprotection, for use in preventing Alzheimer's disease, for use in treating Alzheimer's disease, for use in inhibiting inflammation, for use in protection of the kidney, for use in protection of the liver, for use in preventing or treating cancer, for use in ameliorating a metabolic disorder, for use in preventing diabetes, for use in treating diabetes, for use in treating a bacterial infection, and/or for use in treating depression, a depressive disorder, or major depressive disorder.

The dihydromyricetin (DHM) formulation can be used in the manufacture of a medicament for reducing hangover symptoms, preventing an alcohol use disorder, preventing alcoholism, treating an alcohol use disorder, treating alcoholism, treating an alcohol overdose, neuroprotection, preventing Alzheimer's disease, treating Alzheimer's disease, ameliorating a metabolic disorder, preventing diabetes, treating diabetes, increasing antioxidant capacity, inhibiting inflammation, protecting the kidney, protecting the liver, preventing and/or treating cancer, treating a bacterial infection, and/or treating depression, a depressive disorder, or major depressive disorder.

A method according to the invention for treating a patient suffering from a hangover symptom, an alcohol use disorder, alcoholism, an alcohol overdose, Alzheimer's disease, inflammation, cancer, a metabolic disorder, diabetes, a bacterial infection, and/or depression, a depressive disorder, or major depressive disorder can include administering the dihydromyricetin (DHM) formulation to the patient to reduce the hangover symptom, treat the alcohol use disorder, treat the alcoholism, treat the alcohol overdose, treat the Alzheimer's disease, treat or inhibit the inflammation, treat the cancer, treat or ameliorate the metabolic disorder, treat the diabetes, treat the bacterial infection, and/or treat the depression, depressive disorder, or major depressive disorder.

A method according to the invention for treating a patient at risk of an alcohol use disorder, alcoholism, Alzheimer's disease, inflammation, cancer, a metabolic disorder, and/or diabetes can include administering the dihydromyricetin (DHM) formulation to the patient to prevent the alcohol use disorder, prevent the alcoholism, prevent Alzheimer's disease, prevent the inflammation, prevent the cancer, prevent the metabolic disorder, and/or prevent the diabetes.

A method according to the invention for treating a patient in need of increased antioxidant capacity, neuroprotection, protection of the kidney, and/or protection of the liver can include administering the dihydromyricetin (DHM) formulation to the patient to increase the antioxidant capacity, provide neuroprotection, protect the kidney, and/or protect the liver.

A method according to the invention includes administering the DHM formulation to a patient.

The DHM can be administered to the patient at a dose of from 5 mg to 150 mg DHM per kg patient body weight, at a dose of from 10 mg to 150 mg DHM per kg patient body weight, at a dose of from 50 mg to 100 mg DHM per kg patient body weight, or at a dose of about 75 mg DHM per kg patient body weight.

The permeabilizer can be administered to the patient at a dose of from 5 mg to 300 mg permeabilizer per kg patient body weight, at a dose of from 10 mg to 300 mg permeabilizer per kg patient body weight, at a dose of from 20 mg to 300 mg permeabilizer per kg patient body weight, at a dose of from 10 mg to 200 mg permeabilizer per kg patient body weight, at a dose of from 20 mg to 200 mg permeabilizer per kg patient body weight, at a dose of from 40 mg to 200 mg permeabilizer per kg patient body weight, or at a dose of from 75 mg to 150 mg permeabilizer per kg patient body weight.

5

6

The permeabilizer can be allowed to permeabilize a wall of the patient's intestine and the DHM can be allowed to diffuse into the wall of the patient's intestine and into the patient's bloodstream in administering the DHM to the patient.

The DHM formulation and/or the dosage form can be administered orally to the patient.

The DHM formulation can be administered to the patient as a capsule, the capsule can be allowed to enter the patient's stomach, where the capsule is not dissolved and is not solubilized by gastric juices in the stomach, the capsule can be allowed to pass from the stomach to the patient's intestine, where the capsule is partially or fully dissolved or solubilized by intestinal fluid in the intestine, the partially or fully dissolved or solubilized capsule can be allowed to release the DHM formulation into the intestinal fluid, the permeabilizer can be allowed to permeabilize a wall of the patient's intestine, and the DHM can be allowed to diffuse into a wall of the intestine and into the patient's bloodstream in administering the DHM to the patient.

DETAILED DESCRIPTION OF THE INVENTION

Figure 1:
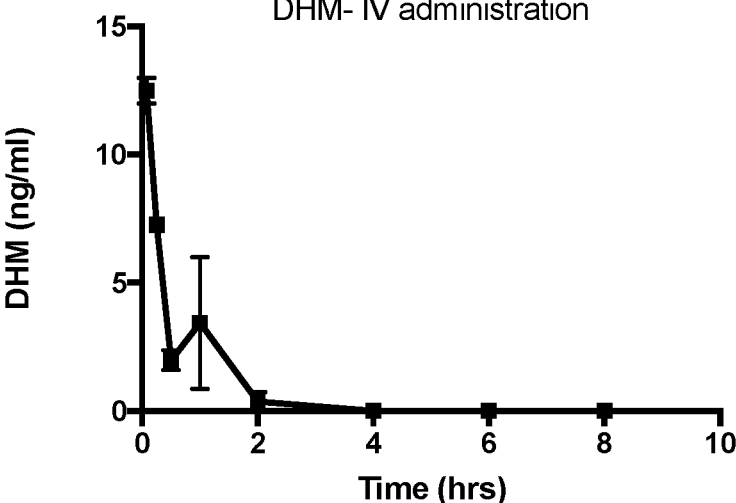
FIG. 1 presents the average blood concentration of dihydromyricetin (DHM) in ng/mL as a function of time in hours (hrs) following intravenous (IV) administration of an average of 1.0 mg of DHM per kg body weight to each rat in a set of rats. The DHM was administered in solution. No sodium caprate (sodium decanoate) was administered. Error bars for each point in time based on the results for each of the rats in the set are shown. The maximum concentration $(C_{max})$ of DHM was 12.5±0.5 ng/mL, and the area under the curve (AUC) of DHM was 11.6±4.9 ng hr/mL.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are hereby incorporated by reference in their entirety as if each had been individually incorporated.

An aspect of the invention comprises a method to improve the bioavailability of the molecule dihydromyricetin (DHM) by co-administering the DHM with a fatty acid and/or a fatty acid salt that may act as a permeability-enhancing compound (permeabilizer). Improvements in bioavailability and pharmacokinetic parameters of DHM can be associated with the inclusion of a fatty acid salt and/or fatty acid that acts as a permeabilizer. The product may include both the DHM and the fatty acid salt and/or fatty acid. Additional compounds, such as additional beneficial molecules, binders, and excipients, such as polymeric excipients may be included in the product. The final form of the product may include powders, granules, or tablets to be used in further formulations. The formulation may be processed further in forms beyond powders, granules, and tablets for administration by various routes either by self-administration or administration by any number of routes known to a skilled artisan. In some embodiments, the formulation may be well suited to oral administration routes. For example, the product may be included in a capsule, tablet, caplet, pill, pastille, troche, or lozenge. Such a capsule, tablet, caplet, pill, pastille, troche, or lozenge may have an enteric coating that, for example, protects the DHM and permeabilizer from conditions of low pH and/or enzymes that may be present in the stomach, mouth, or other parts of the gastrointestinal tract, so that the DHM and permeabilizer reach the intestine in an unaltered or substantially unaltered form. The formulation may be in a liquid form for oral administration in the liquid form, for example, as a liquid, elixir, syrup, liquid solution, suspension, drink, or beverage, or as a liquid concentrate or powder for mixing with water or another liquid to form a liquid for oral administration. The formulation may be in a gel or other semisolid form.

Dihydromyricetin (DHM)

Dihydromyricetin (DHM), a flavonoid compound isolated from the Hovenia plant can "sober-up" rats inebriated with alcohol[2], prevent predisposed rats from becoming alcoholics[2], return alcoholic rats to baseline levels of alcohol consumption[2], reduce hangover symptoms[2], and prevent fetal alcohol spectrum disorders in the offspring of rats exposed to significant amounts alcohol during pregnancy.[2] DHM can be dissolved in a solvent, such as dimethylsulfoxide (DMSO). DHM can be complexed with a metal, such as a divalent alkali earth metal, divalent magnesium (Mg(II), $Mg^{+2}$), a divalent transition metal, divalent iron (Fe(II), $Fe^{+2}$), divalent copper (Cu(II), $Cu^{+2}$), a trivalent transition metal, or trivalent iron (Fe(III), $Fe^{+3}$) DHM has unique physicochemical properties including low solubility, high hydroxyl functional group content, and unknown thermal stability, rendering the processing of DHM and other flavonoids under certain conditions difficult.

DHM demonstrates pharmacological properties for successful medical treatment of alcohol use disorders (AUDs) [21-23]. Given limited available pharmacotherapies for AUDs and these being limited by low patient compliance, because of the adverse effects they may cause, therapies for the treatment of AUDs should be advanced, e.g., through DHM therapeutic strategies.[24]

In addition to DHM's potential for the treatment of AUDs, which, without being bound by theory, may be achieved through DHM's inhibiting the effect of alcohol on $GABA_A$ receptors ($GABA_A$Rs) in the brain, DHM and the Hovenia plant from which it is isolated have shown efficacy in mitigating liver injuries[25-27], decreasing alcohol and acetaldehyde concentrations in the blood via enhancing ADH and ALDH activity[28, 29], and eliminating alcohol-induced excessive free radicals[30]. DHM has been observed to have oxidative stress-mediating activity, i.e., increase antioxidant capacity for scavenging reactive oxygen species, which may result in neuroprotective, nephroprotective (kidney protecting), and hepatoprotective (liver protecting) effects, which may ameliorate, for example, the effects of hypobaric hypoxia, side effects of the chemotherapeutic agent cisplatin, and detrimental effects of ethanol. DHM may have a neuroprotective role in Alzheimer's and Parkinson's diseases. DHM can also inhibit inflammation. DHM can also have anticancer activity and regulate cell proliferation and apoptosis. DHM can mediate metabolism, and may be useful in ameliorating certain metabolic disorders, such as diabetes, weight gain, hyperlipidemia, and atherosclerosis. DHM exhibits antibacterial activity (Li, H. et al., "The Versatile Effects of Dihydromyricetin in Health", Evidence Based Complementary & Alternative Medicine 2017, Art. ID 1 053617). DHM exhibits antidepressive effects, and may be useful in treating or ameliorating conditions or disorders such as depression, depressive disorder, or major depressive disorder (Zhang, J. et al., "Recent Update on the Pharmacological Effects and Mechanisms of Dihydromyricetin", Front. Pharmacol., (Oct. 25, 2018) https://doi.org/10.3389/fphar.2018.01204).

A DHM formulation designed to reduce alcohol's negative effects when taken after alcohol consumption is covered under U.S. Pat. No. 9,603,830 B2 (granted on Mar. 28, 2017) and is sold in the U.S. under the brand name Cheers®.

Despite promising results in rats, one challenge in translating DHM's efficacy to humans in a commercially viable way is DHM's oral bioavailability of less than 5% [31]. DHM can have poor stability. DHM is a Biopharmaceutics Classification System (BCS) class IV drug limited by having the properties of low solubility and low permeability. In the context of successfully commercialized drugs, DHM requires large doses for efficacy. Because DHM is a naturally occurring organic compound isolated from an herb, a DHM formulation can be classified as a food (or dietary supplement) under the Dietary Products designation.

Oral coadministration of DHM with a permeability-enhancing compound (permeabilizer), such as a fatty-acid salt, can improve the oral bioavailability of DHM. For example, oral coadministration of DHM with a permeabilizer can increase the maximum concentration ($C_{max}$), increase the area under the curve (AUC), and increase the bioavailability of DHM over that observed for oral administration of DHM without a permeabilizer. Oral coadministration of DHM with a permeabilizer can decrease the time from administration ($T_{max}$) at which the $C_{max}$ occurs from that observed for oral administration of DHM without a permeabilizer.

For example, DHM can be dosed in a range of from about 0.1, 0.2, 0.5, 1, 2, 5, 10, 20, 30, 40, 50, 60, 70, 75, 80, 90, 100, 110, 120, 130, 140, 150, 160, 180, 200, 250, 300, or 400 mg per kg body weight to about 0.2, 0.5, 1, 2, 5, 10, 20, 30, 40, 50, 60, 70, 75, 80, 90, 100, 110, 120, 130, 140, 150, 160, 180, 200, 250, 300, 400, or 500 mg per kg body weight. For example, DHM can be dosed in a range of from about 1, 2, 5, 10, 20, 30, 40, 50, 60, 70, 75, 80, 90, 100, 110, 120, 130, 140, 150, 160, 180, 200, 250, 300, or 400 mg per kg body weight to about 2, 5, 10, 20, 30, 40, 50, 60, 70, 75, 80, 90, 100, 110, 120, 130, 140, 150, 160, 180, 200, 250, 300, 400, or 500 mg per kg body weight. For example, this dosage can be a daily dose, a weekly dose, or an episodic dose, e.g., before, during, or after the consumption of alcohol.

Permeability Enhancers

A permeability enhancer or permeabilizer is a compound or mixture of compounds that enhance the permeation of a drug compound or an active ingredient through the epithelial cell layer in the gastrointestinal (GI) tract and, hence, enhances, e.g., renders more efficient and/or effective, the amount of active ingredient, e.g., dihydromyricetin (DHM), entering the bloodstream. Permeability-enhancers have been reviewed by Aungst and Whitehead[32-35]. The list of agents presented by Aungst in Table I and Whitehead in Table I are incorporated into this patent in their entirety.

An example of a permeability enhancer is a fatty acid, such as a saturated fatty acid, or a fatty acid salt, such as a saturated fatty acid salt. For example, the fatty acid can be a short-chain fatty acid. For example, the fatty acid can include 4, 5, 6, or 7 carbons. For example, the fatty acid can be a medium-chain, long-chain, or very-long-chain fatty acid. For example, a fatty acid can include 8, 9, 10, 11, 12, 13, 14, 15, 16, 17, 18, 19, or 20 carbons. The salt form (a fatty acid salt) can be a fatty acid bonded with an alkali metal, such as sodium or potassium. Examples of saturated fatty acids and their salts with the number of their carbons (Cn) are the following: C4 (butyric (butanoic) acid, sodium or potassium butyrate (butanoate)); C5 (valeric (pentanoic) acid, sodium or potassium valerate (pentanoate)); C6 (caproic (hexanoic) acid, sodium or potassium caproate (hexanoate)); and C7 (ethanthic (heptanoic) acid, sodium or potassium enanthate (heptanoate)). Examples of saturated fatty acids and their salts with the number of their carbons (Cn) are the following: C8 (caprylic (octanoic) acid, sodium or potassium caprylate (octanoate)); C9 (pelargonic (nonanoic) acid, sodium or potassium pelargonate (nonanoate)); C10 (capric (decanoic) acid, sodium or potassium caprate (decanoate)); C11 (undecylic (undecanoic) acid, sodium or potassium undecanoate); C12 (lauric (dodecanoic) acid, sodium or potassium laurate (dodecanoate)); C13 (tridecylic (tridecanoic) acid, sodium or potassium tridecanoate); C14 (myristic (tetradecanoic) acid, sodium or potassium myristate (tetradecanoate)); C15 (pentadecylic (pentadecanoic) acid, sodium or potassium pentadecanoate); C16 (palmitic (hexadecanoic) acid, sodium or potassium palmitate (hexadecanoate)); C17 (margaric (heptadecanoic) acid, sodium or potassium heptadecanoate); C18 (stearic (octadecanoic) acid, sodium or potassium stearate (octadecanoate)); C19 (nonadecylic (nonadecanoic) acid, sodium or potassium nonadecanoate); and C20 (arachidic (eicosanoic) acid, sodium or potassium arachidate (icosanoate)). For example, a saturated fatty acid is capric acid. Examples of saturated fatty acid salts are sodium caprate (sodium decanoate, $CH_3(CH_2)_8COO^-Na^+$) and potassium caprate (potassium decanoate, $CH_3(CH_2)_8COO^-K^+$). A permeabilizer can be an unsaturated fatty acid or an unsaturated fatty acid salt. A permeabilizer can be a branched fatty acid or a branched fatty acid salt. A permeabilizer can be an unbranched (linear) fatty acid, such as an unbranched (linear), saturated fatty acid, or an unbranched (linear) fatty acid salt, such as an unbranched (linear), saturated fatty acid salt.

For example, the fatty acid or saturated fatty acid can be free in a formulation. Alternatively, the fatty acid or saturated fatty acid can be bonded to glycerol in a triglyceride. For example, the triglyceride can be short chain triglyceride. For example, the triglyceride can be a medium chain, long chain, or very long chain triglyceride. For example, any of the fatty acids bonded to a given triglyceride can be a short chain, medium chain, long chain, and/or very long chain fatty acid and any of the bonded fatty acids can be saturated or unsaturated and can be branched or unbranched (linear). For example, three medium chain fatty acids can be bonded to glycerol in a triglyceride. For example, three medium chain saturated fatty acids can be bonded to glycerol in a triglyceride. For example, decanoic acid (capric acid) can be bonded to glycerol in a triglyceride. For example, three decanoic acid (capric acid) groups can be bonded to glycerol in a medium chain triglyceride.

For example, fatty acids and/or fatty acid salts can be in a medium chain triglyceride formulation, such as a medium chain triglyceride (MCT) formulation derived from coconut oil, palm kernel oil, palm oil, or durian extract; the MCT formulation can be combined with DHM into a DHM formulation. For example, fatty acids, fatty acid salts, and/or triglycerides can be in coconut oil, palm kernel oil, palm oil, or durian extract; the coconut oil, palm kernel oil, palm oil, and/or durian extract can be combined with DHM into a DHM formulation. For example, fatty acids, fatty acid salts, and/or triglycerides can be in a coconut product, such as coconut milk, coconut cream, or coconut butter; the coconut product can be combined with DHM into a DHM formulation.

In a formulation, the mass ratio of permeabilizer (such as sodium caprate) to DHM (permeabilizer:DHM) can range from about 1:100, 1:80, 1:60, 1:50, 1:40, 1:30, 1:25, 1:20, 1:15, 1:12, 1:10, 1:8, 1:7, 1:6, 1:5, 1:4, 1:3, 1:2.5, 1:2, 1:1.67, 1:1.5, 1:1.33, 1:1.2, 1:1.1, 1:1, 1.1:1, 1.2:1, 1.33:1, 1.5:1, 1.67:1, 2:1, 2.5:1, 3:1, 4:1, 5:1, 6:1, 7:1, 8:1, 10:1, 12:1, 15:1, 20:1, 25:1, 30:1, 40:1, 50:1, 60:1, or 80:1 to about 1:80, 1:60, 1:50, 1:40, 1:30, 1:25, 1:20, 1:15, 1:12, 1:10, 1:8, 1:7, 1:6, 1:5, 1:4, 1:3, 1:2.5, 1:2, 1:1.67, 1:1.5, 1:1.33, 1:1.2, 1:1.1, 1:1, 1.1:1, 1.2:1, 1.33:1, 1.5:1, 1.67:1, 2:1, 2.5:1, 3:1, 4:1, 5:1, 6:1, 7:1, 8:1, 10:1, 12:1, 15:1, 20:1, 25:1, 30:1, 40:1, 50:1, 60:1, 80:1, or 100:1.

For example, the permeabilizer can be included with the DHM in the form for administration, so that the permeabilizer is dosed in a range of from about 0.1, 0.2, 0.5, 1, 5, 10, 20, 30, 40, 50, 60, 70, 75, 80, 90, 100, 110, 120, 130, 140, 150, 160, 180, 200, 250, 300, 400, 500, 600, 800, 1000, or 1500 mg per kg body weight to about 0.2, 0.5, 1, 5, 10, 20, 30, 40, 50, 60, 70, 75, 80, 90, 100, 110, 120, 130, 140, 150, 160, 180, 200, 250, 300, 400, 500, 600, 800, 1000, 1500, or 2000 mg per kg body weight. For example, this dosage can be a daily dose, a weekly dose, or an episodic dose, e.g., before, during, or after the consumption of alcohol.

Excipients and Matrix Materials

Excipients and matrix materials are defined as materials that aid in the formulation, stability, and/or release characteristics of the active molecule DHM. For example, homopolymers, copolymers, and amphiphilic copolymers can be used as excipients and matrix materials. Excipients may be blended or otherwise physically mixed with DHM. A solid dispersion may also be prepared comprising DHM dispersed in a matrix material, with the DHM remaining substantially crystalline or substantially amorphous in nature. The matrix material can constitute from 0.1 wt % to 99 wt % of the combined mass of the active agent(s) and excipients by weight of the final solid form. When it is desirable for the matrix material to prevent aggregation of the active domains into larger aggregates, the matrix material can constitute more than 20% or more than 40% of the combined mass of the active agent(s) and matrix material. For example, the matrix material can constitute from 0.01, 0.02, 0.05, 0.1, 0.2, 0.5, 1, 2, 5, 10, 20, 30, 40, 50, 60, 70, 80, 90, 95, 98, or 99 wt % to 0.02, 0.05, 0.1, 0.2, 0.5, 1, 2, 5, 10, 20, 30, 40, 50, 60, 70, 80, 90, 95, 98, 99, or over 99 wt % of the combined mass of the active agent(s) and excipients by weight of the final solid form. For example, the DHM and a permeabilizer can be dispersed in a matrix material through a hot melt extrusion process. For example, the DHM and a permeabilizer can be dispersed in a matrix material through a spray drying process (to form a spray-dried dispersion (SDD) powder). For example, the DHM and/or the permeabilizer can be molecularly dispersed in the matrix material. The DHM can be amorphous in the matrix material.

Exemplary excipients and matrix materials include low melting point waxes such as carnauba wax, cellulose, methyl cellulose, ethyl cellulose, polyvinylpyrrolidone (PVP) and its copolymers such as polyvinylpyrrolidone-vinyl acetate (PVP-VA), poly(ethylene-co-vinyl acetate), various grades of polyethylene glycol (PEG), polyethylene oxide (PEO), cellulose esters, cellulose acrylates, cellulose derivatives, polymethacrylate, polymethacrylate derivatives, polyoxyethylene-polyoxypropylene block copolymers (also referred to as poloxamers), hydroxypropylcellulose (HPC), hydroxypropyl methylcellulose (HPMC), HPMC derivatives, polylactic acid (PLA), poly(glycolide) (PGA), and poly(lactide-co-glycolide) (PLGA), poly(caprolactone) (PCL), starch, starch derivatives, sugars, sugar alcohols, waxes, leucine, lipids, carboxymethylcellulose, sodium carboxymethylcellulose, carboxymethylcellulose salts, hydroxyethylcellulose, methacrylic acid copolymers, poly(methyl methacrylate) (PMMA), and ethylene glycol-vinyl glycol copolymer.

For example, an excipient and matrix material can be a poly(vinyl acetate-co-vinyl caprolactam-co-ethylene oxide), such as a polyethylene oxide polymer grafted with poly (vinyl acetate) and poly(vinyl caprolactam) (Soluplus®).

Examples of excipients and matrix materials include polyoxyethylene alkyl ethers, polyoxyethylene castor oils, polycaprolactam, hydroxypropyl methyl cellulose acetate succinate (HPMCAS), hydroxypropyl methyl cellulose propionate succinate, hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, carboxymethyl ethylcellulose (CMEC), hydroxypropyl methylcellulose (HPMC), hydroxypropyl methylcellulose acetate phthalate (HPMCAP), hydroxypropyl methylcellulose propionate phthalate, hydroxypropyl methylcellulose acetate trimellitate (HPMCAT), hydroxypropyl methylcellulose propionate trimellitate, cellulose acetate succinate (CAS), methyl cellulose acetate succinate (MCAS), poly(methacrylic acid-co-methyl methacrylate) 1:1 (e.g., Eudragit® L100, Evonik Industries AG), poly(methacrylic acid-co-methyl methacrylate) 1:2 (e.g., Eudragit® S100), poly (methacrylic acid-co-ethyl acrylate) 1:1 (e.g., Eudragit® L100-55), a polyol, a polyether, a cellulosic polymer, sugars and sugar alcohols, for example, fructose, glucose, lactose, mannitol, trehalose, sucrose, raffinose, maltitol, lactitol, sorbitol, xylitol, erythritol, xylose, acorbose, melezitose, galactose, melibrose, and isomaltose, natural sugar extracts, for example, malt beet sugar, corn sugar, high-fructose corn syrup, sugar oligomers, such as polydextrose and dextrans with molecular weights less than 10,000 Daltons, polyols such as glycerol, sorbitol, ethylene glycol, propylene glycol, butanediol, and other oligomers, low molecular-weight oligomers, such as low molecular weight polyethylene glycol and low molecular weight poly(methyl methacrylate), ethoxylated castor oil, polyoxyl hydrogenated castor oil, polyoxyl 40 hydrogenated castor oil, polymeric derivatives of vitamin E, polyethoxylated sorbitan, and polyoxyethylene sorbitan monooleate.

The excipients and matrix materials can include amphiphilic block copolymers, for example, polystyrene-block-polyethylene glycol (PS-b-PEG), polylactic acid-block-polyethylene glycol (PLA-b-PEG), and poly(lactic-co-glycolic acid)-block-polyethylene glycol (PLGA-b-PEG).

Examples of excipients and matrix materials include derivatives of the above, copolymers of the above, and combinations of the above.

In an embodiment, the matrix material includes components with a molecular weight of less than 1,000,000 Daltons (Da), less than 100,000 Daltons, less than 10,000 Daltons, less than 5000 Daltons, or less than 2000 Daltons.

The matrix material can include a polymer. A polymer is formed of several monomer units bound to each other. For example, a polymer can be a linear polymer, a branched polymer, or a cyclic polymer. In a cyclic polymer, a set of monomers can be bound to each other to form a ring. In a noncyclic polymer, there is no set of monomers that are bound to each other to form a ring (although atoms within a given monomer unit of the polymer still may be in a ring structure, e.g., a cyclopentyl, furan, furanose, cyclohexyl, pyran, pyranose, benzene, or saccharide structure). For example, cyclodextrin is a cyclic polysaccharide. By contrast, cellulose is a linear polysaccharide formed of several hundred to many thousands of D-glucose monomers. Gum arabic includes arabinogalactan, formed of arabinose and galactose monomers.

Certain polymeric excipients and matrix materials marketed under trade names by manufacturers may include the following: BASF: Povidones, copovidones, methacrylic acid copolymers, ethylene glycol-vinyl glycol copolymers, Poloxamer 407, Poloxamer 188, poly ethylene glycols, polyoxyl 40 hydrogenated castor oils, and polymeric derivatives of vitamin E marketed by BASF under trade names SOLUPLUS, KOLLIDON VA 64, KOLLIDON 12 PF, KOLLIDON 17 PF, KOLLIDON 30, KOLLIDON 90 F, KOLLIDON SR, KOLLICOAT MAE 100P, KOLLICOAT IR, KOLLICOAT PROTECT, KOLLIPHOR P 407, KOLLIPHOR P407 MICRO, KOLLIPHOR P188, KOLLIPHOR P188 MICRO, KOLLISOLV PEG, KOLLIPHOR RH 40, KOLLIPHOR TPGS.

The Dow Chemical Company: Polymers with trade names METHOCEL, ETHOCEL, POLYOX, and AFFINISOL marketed by the Dow Chemical Company.

Evonik Corporation: Polymers with trade names EUDRAGIT (methacrylates) and RESOMER, marketed by Evonik Corporation.

Ashland: Polymers with trade names AquaSolve hypromellose acetate succinate, Aqualon ethylcellulose, Aqualon sodium carboxymethylcellulose, Aquarius control film coating systems, Aquarius prime film coating systems, Aquarius protect film coating systems, Aquarius film coating systems, Aquarius preferred film coating systems, Benecel methylcellulose and hypromellose, Blanose sodium carboxymethylcellulose, CAVAMAX native cyclodextrins, Cavitron cyclodextrin, CAVASOL cyclodextrin, Klucel hydroxypropylcellulose, Natrosol hydroxyethylcellulose, Pharmasolve N-methyl-2-pyrrolidone, Plasdone S-630 copovidone, Plasdone povidone, and Polyplasdone crospovidone (cross linked polyvinyl N-pyrrolidone) marketed by Ashland Global Holdings Inc.

The foregoing lists of materials are not intended to indicate that all of these materials are equivalent and/or equally suitable.

The polymer matrix material can have a glass transition temperature (Tg) of at least 60° C., 70° C., 80° C., 90° C., 100° C., 110° C., 115° C., 120° C., 125° C., 130° C., 150° C., 175° C., 200° C., or 250° C. For example, hydroxypropyl methyl cellulose acetate succinate (HPMCAS) has a glass transition temperature (Tg) of about 120° C. For example, polyethylene oxide polymer grafted with poly(vinyl acetate) and poly(vinyl caprolactam) (Soluplus®) has a glass transition temperature (Tg) of about 70° C.

The polymer matrix material may be selected to adjust the formulation's release profile, e.g., to adjust the rate at and duration of time over which the formulation releases an active pharmaceutical ingredient (API), such as DHM.

In an embodiment, polymers, such as one or more of those listed above, may also be incorporated as enteric coatings which coat a final capsule, tablet, or other solid form of a DHM formulation and provide additional stability or sustained release benefits. For example, including an enteric coating in the formulation may alter the formulation's release profile, e.g., may alter the rate at and duration of time over which the formulation releases an active pharmaceutical ingredient (API), such as DHM. For example, the enteric coating may be a methacrylate copolymer coating.

Administration

The resulting formulations of embodiments of the invention are useful and suitable for delivery in animals and humans and may be administered by, for example, oral administration. Such methods of administration and others contemplated within the scope of the invention are known to the skilled artisan. In vivo stability of the present formulation may vary according to the physiological environment to which it is exposed and the matrix material and excipients. Therefore, the necessity for or frequency of re-administration may be different for various formulations.

A formulation of an embodiment of the invention may be provided in a variety of ways, for example, in a powder, suspension, gel cap, capsule, tablet, caplet, pill, pastille, troche, or lozenge form. Additional components may be added to the formulation prior to formation into its final form.

In solid dosage forms, the compounds can be combined with conventional carriers, for example, one or more of the following: binders, such as acacia, corn starch, or gelatin; disintegrating agents, such as corn starch, guar gum, potato starch, or alginic acid; lubricants, such as stearic acid or magnesium stearate; and inert fillers, such as lactose, sucrose, or corn starch.

It is contemplated that either one or a combination of long-acting, sustained-release, controlled-release, and/or or slow-release dosage forms may be used in an embodiment of the invention. This may be desirable, if continuous exposure of an animal or a human to the active ingredient(s) (e.g., DHM) is the desired outcome. The polymers and formulations useful in this case can include derivatized cellulosic polymers of the type described in the Dow Chemical Company Technical Bulletin "Using Dow Excipients for Controlled Release of Drugs in Hydrophilic Matrix Systems", 2006 and marketed under the trade name METHOCEL (methylcellulose and hydroxypropyl methylcellulose (HPMC) polymers). The course and duration of administration of and the dosage requirements for the formulation of an embodiment of the invention will vary according to the animal or human being treated, the formulation used, the method of administration used, the severity of the condition being treated, the coadministration of other drugs and/or active ingredients, and other factors.

Increased bioavailability may be achieved by tuning the interactions between the active ingredient (e.g., DHM) and a matrix. For example, the active ingredient (e.g., DIM) can be substantially soluble in a molten polymer phase of a matrix, which can include one or more excipient(s), such that upon cooling and solidification, that active ingredient is prevented from substantially crystallizing. Alternatively, DHM may be dissolved along with an excipient in a suitable solvent, and the solution may be rapidly dried and solidified (e.g., via spray drying) to yield a solid dispersion, such that the active ingredient is prevented from substantially crystallizing. Capturing the active ingredient (e.g., DHM) in an amorphous, or non-crystalline-associated state (which can be a high-energy state), can result in a higher dissolution level or a supersaturation level, when dissolved in vitro or in vivo. Thermodynamic reasons for this increase in solubility have been discussed by Hu, Johnson & Williams[36].

Commercially supplied pure DHM can be entirely (100%) or nearly entirely crystalline.

The crystallinity of the DHM in the formulation can be qualitatively assessed or quantitatively measured by techniques, such as polarized light microscopy (PLM), differential scanning calorimetry (DCS), and powder X-ray diffraction (P-XRD). The DHM in the formulation can have a crystallinity of at least 99%, 98%, 95%, 90%, 80%, 60%, 50%, 40%, 30%, 20%, 25%, 20%, 15%, 10%, 7%, 5%, 3%, 2%, or 1%. The DHM can be substantially amorphous. The DHM can be amorphous.

The formulation of an embodiment of the invention may be in a liquid form for oral administration in the liquid form, for example, as a liquid, elixir, syrup, liquid solution, suspension, drink, or beverage, or as a liquid concentrate or powder for mixing with water or another liquid to form a liquid for oral administration. The formulation may be in a gel or other semisolid form.

Capsules and Gel Capsules

A gel capsule is a soft-shelled capsule, which allows for efficient encapsulation and administration of formulations including an active ingredient, such as DHM, along with other ingredients, such as a fatty-acid permeabilizer. A gel capsule may also be referred to as a "soft gel capsule", "softgel capsule", "gel cap", or "gelcap".

Gel capsules may be easier to swallow, avoid dust handling issues, and have increased stability compared to other dosage forms. Gel capsules may be filled with a liquid. Soft gel capsules provide an exemplary route for encapsulation and administration of the formulation containing DHM and a permeabilizer. Gel capsules may be produced from animal sources (e.g., gelatin), algal sources, vegetable sources (e.g., hypromellose (hydroxylpropyl methylcellulose, HPMC)), or synthetic sources (e.g., polyvinyl alcohol (PVA) and polyethylene glycol (PEG)). Additional examples of materials for producing gel capsules include a polysaccharide, a sulfated polysaccharide, a carrageenan, cellulose, a cellulose derivative, starch, a starch derivative, pullulan, and polyvinyl alcohol (PVA) copolymer. For example, the capsule or gel capsule may be of or include material of algal origin; i.e., the material of which the wall of the capsule is formed may be of or include material of algal origin or derived from an algal material. These and combinations of these and other materials may be used to form a gel capsule (or a capsule). The gel capsules may be filled with an oil containing DHM and an emulsifier (surfactant) and/or other excipients. The gel capsules may be filled with a liquid or a gel containing DHM. The gel capsules may be filled with a solid, e.g., a powder, containing DHM.

The material of which the gel capsule or capsule is formed may be selected to not dissolve or solubilize at low pH (e.g., pH of at most (i.e., less than or equal to) 4.8, 4.5, 4, 3.5, 3.2, 3, 2.7, 2.5, 2.3, 2, 1.8, 1.5, or 1), such as found in the acidic environment of the stomach. The material of which the gel capsule or capsule is formed may be selected to dissolve or solubilize at near neutral, neutral, or greater than neutral (alkaline) pH, e.g., pH of at least (i.e., greater than or equal to) 5, 5.3, 5.5, 5.8, 6, 6.2, 6.5, 6.7, 7, 7.2, or 7.5, such as found in the intestine. The material of which the gel capsule or capsule is formed may be selected to not dissolve or solubilize in hydrophobic, lipophilic, and/or nonpolar liquids, such as an oil. The material of which the gel capsule or capsule is formed may be selected to dissolve or solubilize in hydrophilic and/or polar liquids, such as water or an aqueous solution. The material of which the gel capsule or capsule is formed may be selected to alter or control the dissolution or solubilization of the gel capsule or capsule, e.g., to alter the rate at and duration of time over which the gel capsule or capsule dissolves or solubilizes to release its contents, e.g., a pre-emulsion composition including an active ingredient (e.g., DHM).

Enteric Coating

Enteric coatings can be polymers, such as cellulosic compounds, that are applied to the outside of a solid dosage form such as a capsule, gel capsule, tablet, caplet, pill, pastille, troche, or lozenge and provide an additional barrier to modify the release characteristics of the contents therein.

Examples of enteric polymers for use on container coatings include shellac, cellulose acetate trimellitate (CAT), various hydroxypropyl cellulose polymers (i.e., HPMC, HPMCP, HPMCAS), and phthalates such as cellulose acetate phthalate (CAP) and polyvinyl acetate phthalate (PVAP). Pros and cons exist for each polymer. Shellac, a natural product derived from an insect secretion, may be subject to inconsistent supply and unacceptable variations in quality. Cellulose acetate trimellitate may require the potentially undesirable addition of ammonium hydroxide (Wu et al., U.S. Pat. No. 5,851,579). Hydroxypropylcellulose (HPC) polymers may be unstable upon longer term storage, particularly under conditions of high humidity. Further examples of polymers used to achieve enteric properties in container coatings include anionic polymethacrylates (copolymers of methacrylic acid and either methyl methacrylate or ethyl acrylate) (EUDRAGIT®) such as EUDRAGIT® L 30 D-55 (Methacrylic Acid Copolymer Dispersion, NF), which is soluble at a pH above about 5.5. [44]

The material of which the enteric coating is formed may be selected to not dissolve or solubilize at low pH (e.g., pH of at most (i.e., less than or equal to) 4.8, 4.5, 4, 3.5, 3.2, 3, 2.7, 2.5, 2.3, 2, 1.8, 1.5, or 1), such as found in the acidic environment of the stomach. The material of which the enteric coating is formed may be selected to dissolve or solubilize at near neutral, neutral, or greater than neutral (alkaline) pH, e.g., pH of at least (i.e., greater than or equal to) 5, 5.3, 5.5, 5.8, 6, 6.2, 6.5, 6.7, 7, 7.2, or 7.5, such as found in the intestine. The material of which the enteric coating is formed may be selected to not dissolve or solubilize in hydrophobic, lipophilic, and/or nonpolar liquids, such as an oil. The material of which the enteric coating is formed may be selected to dissolve or solubilize in hydrophilic and/or polar liquids, such as water or an aqueous solution. The material of which the enteric coating is formed may be selected to alter or control the dissolution or solubilization of a gel capsule or capsule that it coats, e.g., to alter the rate at and duration of time over which the gel capsule or capsule dissolves or solubilizes to release its contents, e.g., a pre-emulsion composition including an active ingredient (e.g., DHM).

Liquid Dosage Form

Dihydromyricetin (DHM) and a permeabilizer can be formulated into a liquid dosage form for oral administration, such as a liquid, elixir, syrup, liquid solution, suspension, drink, or beverage, or as a liquid concentrate or powder for mixing with water or another liquid to form a liquid for oral administration. The liquid dosage form can be an aqueous liquid. The DHM can be dissolved, emulsified, dispersed as a suspension, and/or dispersed as a colloid in the aqueous liquid. The DHM can be dissolved in water up to its solubility limit. A greater concentration of DHM can be incorporated into an aqueous liquid by also including a cosolvent, surfactant, or emulsifier. Examples of cosolvents are glycerol, propylene glycol, sugar alcohols (e.g., sorbitol, mannitol, erythritol, xylitol, lactitol, maltitol, etc.), and ethanol. Surfactants and emulsifiers can be used that are of plant origin or plant derived, such as carrageenan, guar gum, and xanthan gum, lecithin, lactylates, and sodium stearoyl-2-lactate, that are of animal origin or animal derived, and that are synthetically or semi-synthetically produced, such as polysorbates (e.g., Tween 20, Tween 40, Tween 60, Tween 80, etc.), sorbitan monostearate (Span 60), sorbitan monolaurate (Span 20), and sorbitan tristearate (Span 65). The DHM can also be dispersed into the aqueous liquid as a suspension or colloid, and surfactants, emulsifiers, and polymers can be used to stabilize the suspension or colloid. Examples of polymers that can stabilize the suspension or colloid include, but are not limited to poly(vinylpyrrolidone) (PVP) and poly(vinylpyrrolidone-co-vinyl acetate) (PVP-VA). Examples of polymers that can stabilize the suspension or colloid include, but are not limited to a cellulosic polymer, hydroxypropyl methylcellulose (HPMC), hydroxypropyl methylcellulose acetate succinate (HPMCAS), and carboxymethyl cellulose (CMC). A biocompatible water soluble polymer can stabilize the suspension or colloid. A cyclodextrin (e.g., beta-cyclodextrin) can promote solubility of the DHM, for example, increase the amount of DHM that can be dissolved in a given volume of aqueous liquid. The permeabilizer, such as a fatty acid, fatty acid salt, or triglyceride can act as a cosolvent or surfactant.

The concentration of the DHM in the liquid dosage form can be, for example, at least 0.001 wt % DHM, 0.002 wt % DHM, 0.005 wt % DHM, 0.01 wt % DHM, 0.02 wt % DHM, 0.04 wt % DHM, at least 0.07 wt % DHM, at least 0.1 wt % DHM, at least 0.14 wt % DHM, at least 0.2 wt % DHM, at least 0.4 wt % DHM, at least 1 wt % DHM, at least 2 wt % DHM, at least 3 wt % DHM, at least 4 wt % DHM, at least 5 wt % DHM, at least 6 wt % DHM, at least 7 wt % DHM, or at least 8 wt % DHM.

Cysteine (e.g., L-cysteine) can be included in the liquid dosage form. For example, L-cysteine can reduce acetaldehyde concentrations in the gut (the intestines). The concentration of cysteine in the liquid dosage form can be, for example, at least 0.01 wt % cysteine, 0.02 wt % cysteine, at least 0.05 wt % cysteine, at least 0.1 wt % cysteine, at least 0.2 wt % cysteine, at least 0.3 wt % cysteine, at least 0.5 wt % cysteine, or at least 1 wt % cysteine.

Carbon dioxide ($CO_2$) can be included in the liquid dosage form ("carbonation"). For example, carbon dioxide can be introduced into the liquid dosage form at a concentration that this greater than the solubility limit of carbon dioxide in the liquid dosage form at the temperature (e.g., 25° C. or less) and pressure (e.g., 1 atmosphere) at which the liquid dosage form is to be consumed or ingested, so that the liquid dosage form is effervescent (bubbles of carbon dioxide form) when the liquid dosage form is consumed or ingested. Such carbonation may increase the rate at which DHM and permeabilizer passes from the stomach to the small intestine, resulting in an increase in the rate at which the DHM enters the bloodstream. The concentration of carbon dioxide in the liquid dosage form can be, for example, at least 0.1 wt % carbon dioxide, at least 0.3 wt %, at least 0.5 wt % carbon dioxide, at least 0.8 wt % carbon dioxide, or at least 1.5 wt % carbon dioxide.

Other compounds and substances that can be included in the liquid dosage form include, for example, prickly pear, milk thistle, flavoring agents (natural and artificial), sweeteners, such as natural sugars, e.g., glucose, fructose, and sucrose, sugar alcohols, e.g., sorbitol, mannitol, erythritol, xylitol, lactitol, and maltitol, and artificial sweeteners, e.g., aspartame, tartness agents, e.g., citric acid, electrolytes, e.g., sodium chloride, sodium citrate, and potassium chloride, to play an oral rehydration role, and vitamins, e.g., one or more B vitamins (vitamin $B_1$ (thiamine), vitamin B2 (riboflavin), vitamin B3 (niacin (nicotinic acid), nicotinamide, and/or nicotinamide riboside), vitamin B5 (pantothenic acid), vitamin B6 (pyridoxine, pyridoxal, and/or pyridoxamine), vitamin B7 (biotin), vitamin B9 (folate), and/or vitamin B12 (cobalamin, cyanocobalamin, and/or methylcobalamin)), vitamin C (ascorbic acid), and vitamin E (tocopherols and tocotrienols).

The pH of the liquid dosage form can be adjusted to a desired amount, for example, by adding acidic agents such as citric acid. For example, the pH of the liquid dosage form can be adjusted to at most 7 (less than or equal to 7), at most 6 (less than or equal to 6), at most 5 (less than or equal to 5), at most 4 (less than or equal to 4), at most 3 (less than or equal to 3), or at most 2 (less than or equal to 2).

A compound or substance in the liquid dosage form can serve more than one function. For example, glycerol can function as both a cosolvent and a sweetener. For example, carbon dioxide can function as an agent to increase the rate of uptake (from the time of ingestion or consumption of the liquid dosage form) into the bloodstream, function to enhance the taste experience by the patient or consumer, and function to lower the pH of the liquid dosage form. For example, a fatty acid or a fatty acid salt, such as capric acid or sodium caprate, can function as a permeabilizer and as a surfactant. For example, sodium citrate can function to promote oral rehydration, to adjust taste (tartness), and as a surfactant.

For example, a liquid dosage form can include the following in water:

at least 0.14 wt % dihydromyricetin (DHM);
at least 0.3 wt % capric acid;
0.06 wt % L-cysteine; and
(optionally) 0.6 wt % carbon dioxide.

Dissolution Kinetics Studies

In an embodiment, the DHM in the form for administration, e.g., a powder, suspension, gel cap, capsule, tablet, caplet, pill, pastille, troche, or lozenge form, does not dissolve in and/or is not solubilized by an aqueous solution having a pH of at most (i.e., less than or equal to) 4.8, 4.5, 4, 3.5, 3.2, 3, 2.7, 2.5, 2.3, 2, 1.8, 1.5, or 1. The chyme that is expelled by the stomach, through the pyloric valve, has a pH of approximately 2. Gastric juices lead to material in the stomach having a pH in the range of from 1.5 to 3.5, and this low pH in the stomach and the enzymes active in the stomach at this low pH may result in degradation of DHM and quenching of DHM activity.

In an embodiment, the DHM in the form for administration dissolves in and/or is solubilized by water (pH of 7) and/or an aqueous solution having a pH of at least (i.e., greater than or equal to) 5, 5.3, 5.5, 5.8, 6, 6.2, 6.5, 6.7, 7, 7.2, or 7.5. Bile released into the duodenum and/or pancreatic secretions of sodium bicarbonate increase the pH of the chyme. For example, the pH of chyme and material in the intestine (bowel) can range from 5.5 to 7, for example, can be 7. The dissolution and/or solubilization of the DHM in the spray-dried dispersion powder in the intestine, for example, the small intestine, can result in the DHM being absorbed by the wall of the intestine, for example, the wall of the small intestine, and into the blood.

For example, hydroxypropyl methyl cellulose acetate succinate (HPMCAS) is insoluble in an aqueous solution of acidic (low) pH, but is soluble in an aqueous solution of neutral or alkaline (high) pH. Therefore, a form for administration including HPMCAS and DHM can retain the DHM at an acidic (low) pH, e.g., a pH of 3.5 or less, but release the DHM at a neutral or alkaline (high) pH, e.g., a pH of 7 or greater.

A pH buffering agent can be included in such a form for administration.

Inclusion of an acidic component in such a form for administration, such as an acidic pH buffering agent (i.e., a buffering agent that maintains an acidic pH, a pH of less than 7), e.g., citric acid or a citrate salt (e.g., a sodium citrate, a potassium citrate, calcium citrate, and/or combinations), can stabilize an aqueous solution formed with the form for administration, so that the DHM is not released into the aqueous solution or so that the release of the DHM into the aqueous solution is delayed.

The polymer matrix material can be selected, so that it is moderately soluble (e.g., from 0.01 g/100 mL to 3 g/100 mL, or from 0.1 g/100 mL to 1 g/100 mL) in water. Moderate solubility in water allows the polymer matrix material to dissolve in the body of an organism and release the DHM.

The dissolution and release kinetics of DHM are studied under different conditions; three protocols are described as follows.[37]

Release Kinetics in Vitro: Simulated gastric fluid (FaSSGF (fasted state simulated gastric fluid)) and intestinal fluids (FaSSIF (fasted state simulated intestinal fluid) and FeSSIF (fed state simulated intestinal fluid)) are prepared according to the manufacturer's instructions. Each formulation is evaluated in triplicate with a release medium swap assay. Additionally, dissolution tests are also performed with the DIM-containing form for administration with the appropriate controls.

Release under Gastric Conditions: DHM-containing powder samples are suspended in prewarmed FaSSGF (37° C.) to achieve an active ingredient concentration of ~75 µg/mL by pipetting up and down vigorously multiple times. The samples are incubated at 37° C. (NesLab RTE-111 bath circulator, Thermo Fisher Scientific, Waltham, MA) for 30 min without agitation to mimic physiological gastric conditions and transition time in the stomach. Aliquots are taken at 1, 5, 10, 15, 20, and 30 min. To analyze the free DHM concentration, each aliquot is centrifuged at 28000 g for 5 min to pellet suspended particles. The supernatant is diluted further with FaSSGF to fall within the calibration range, and DHM concentration is determined with a UV-Vis spectrometer at 290 nm.

Release under Intestinal Conditions: DHM-containing powder samples are suspended in prewarmed FaSSIF or FeSSIF (37° C.) to achieve an active ingredient concentration of roughly 10× the equilibrium solubility of DUM in the respective medium (previously determined) by pipetting up and down vigorously multiple times. The samples are incubated at 37° C. (NesLab RTE-111 bath circulator, Thermo Fisher Scientific, Waltham, MA) without agitation to mimic physiological gastric conditions. Aliquots are taken at 1, 5, 10, 15, 30, 60, 120, and 360 min. To analyze the free DHM concentration, each aliquot is centrifuged at 28000 g for 5 min to pellet suspended particles. The supernatant is removed, frozen, and lyophilized to isolate the dissolved solids. Each sample is reconstituted with organic solvent, diluted as needed to fall within calibration range, and analyzed by HPLC with UV-vis detection at 290 nm. DHM concentration is calculated based on a calibration curve.

For example, the dissolution kinetics of DHM in a form for administration in an embodiment of the invention in in vitro dissolution tests in simulated fasted state fluid can be increased by 5%, 10%, 15%, 20%, 30%, 40%, 50%, 60%, 100%, 250% after 15 minutes over that of pure DHM.

For example, the dissolution kinetics of DHM in a form for administration in an embodiment of the invention in in vitro dissolution tests in simulated fed state fluid can be increased by 5%, 10%, 15%, 20%, 30%, 40%, 50%, 60%, 100%, 250% after 15 minutes over that of pure DHM.

For example, the dissolution kinetics of DHM in a form for administration in an embodiment of the invention in in vitro dissolution tests in simulated fasted state fluid can be increased by 5%, 10%, 15%, 20%, 30%, 40%, 50%, 60%, 100%, 250% after 30 minutes over that of pure DHM.

For example, the dissolution kinetics of DHM in a form for administration in an embodiment of the invention in in vitro dissolution tests in simulated fed state fluid can be increased by 5%, 10%, 15%, 20%, 30%, 40%, 50%, 60%, 100%, 250% after 30 minutes over that of pure DHM.

Animal Pharmacokinetic (PK) Studies

Dihydromyricetin (DHM) can be administered to an animal (e.g., a rat or a mouse), for example, as DHM dissolved in water, saline, or another liquid or as a DHM crystalline, semicrystalline, or amorphous powder. The DHM can be administered intravenously or orally, e.g., as an oral gavage or in a capsule, tablet, caplet, pill, pastille, troche, or lozenge or in a liquid form. Orally-administered DHM can be administered together with a fatty acid salt or a fatty acid that may act as a permeabilizer. A pharmacokinetic study can be carried out to evaluate animal pharmacokinetics. Blood samples can be collected from the animal at predetermined time intervals from the administration of the DHM. The (blood) plasma concentration of DHM in a sample can be determined, for example, using a Waters Acquity ultra performance liquid chromatography system equipped with an electrospray ionization mass spectrometry system (Waters, Milford, MA), in accordance with a previous report [38], or an equivalent or alternative analytical system.

For example, the blood concentration of dihydromyricetin (DHM) after oral administration together with a permeabilizer to a human or an animal can be as follows. The maximum concentration ($C_{max}$) of DHM in the blood can be in the range of from about 1, 5, 10, 15, 20, 25, 30, 35, 40, 45, 50, 60, 70, 80, 100, 120, 150, 200, 250, 300, 400, 500, 600, 800, 1000, 1500, 2000, 2500, 3000, 3500, 4000, 5000, 6000, 8000, 10000, 12000, or 15000 ng/mL to about 5, 10, 15, 20, 25, 30, 35, 40, 45, 50, 60, 70, 80, 100, 120, 150, 200, 250, 300, 400, 500, 600, 800, 1000, 1500, 2000, 2500, 3000, 3500, 4000, 5000, 6000, 8000, 10000, 12000, 15000, or 20000 ng/mL. The time ($T_{max}$) from administration to the maximum concentration of DHM in the blood can be in the range of from about 3, 5, 10, 15, 20, 25, 30, 35, 40, 45, 50, or 55 minutes (mins) or 1, 1.5, 2, 2.5, 3, 3.5, 4, 5, 6, 7, 8, 10, 12, or 15 hours (hrs) to about 5, 10, 15, 20, 25, 30, 35, 40, 45, 50, or 55 minutes (mins) or 1, 1.5, 2, 2.5, 3, 3.5, 4, 5, 6, 7, 8, 10, 12, 15, or 20 hours (hrs). The area under the curve (AUC) of DHM in the blood can be in the range of from about 10, 20, 50, 100, 150, 200, 250, 300, 350, 400, 450, 500, 600, 800, 1000, 1200, 1500, 2000, 3000, 4000, 5000, 6000, 7000, 8000, 10000, 12000, 15000, 20000, or 25000 ng hr/mL to about 20, 50, 100, 150, 200, 250, 300, 350, 400, 450, 500, 600, 800, 1000, 1200, 1500, 2000, 3000, 4000, 5000, 6000, 7000, 8000, 10000, 12000, 15000, 20000, 25000, or 30000 ng hr/mL. The bioavailability ($F_{abs}$) of DHM in the blood can be defined as $$F_{abs} = 100 \frac{AUC_{oral}/D_{oral}}{AUC_{IV}/D_{IV}}$$

where $AUC_{oral}$ and $D_{oral}$ indicate the AUC and dosage for a given oral administration, and $AUC_{IV}$ and $D_{IV}$ indicate the AUC and dosage for an intravenous (IV) administration, for example, an intravenous administration of 1 mg DHM per kg body weight. The bioavailability ($F_{abs}$) of DHM in the blood can be from about 1, 2, 5, 10, 15, 20, 25, 30, 35, 40, 45, 50, 60, 80, 100, 120, 150, 200, 300, 400, 500, 600, 700, 800, 1000, 1200, 1500, 2000, or 2500 to about 2, 5, 10, 15, 20, 25, 30, 35, 40, 45, 50, 60, 80, 100, 120, 150, 200, 300, 400, 500, 600, 700, 800, 1000, 1200, 1500, 2000, 2500, or 3000.

EXPERIMENTAL EXAMPLES

Example 1: Pharmacokinetic (PK) Data from Intravenous (IV) Administration of Dihydromyricetin (DHM)

An average of 1.0 mg of dihydromyricetin (DHM) per kg body weight was intravenously administered to each rat in a set of three (3) Sprague-Dawley rats. The DHM was administered in an 0.9% saline solution. No sodium caprate (sodium decanoate, Na caprate) was administered. A blood sample was collected from each rat at predetermined times and analyzed with LC-MS/MS (liquid chromatography tandem mass spectrometry). FIG. 1 presents the average blood concentration of dihydromyricetin (DHM) in ng/mL as a function of time in hours (hrs) following administration. Error bars for each point in time based on the results for each of the rats in the set are shown. The maximum concentration ($C_{max}$) of DHM was 12.5±0.5 ng/mL, and the area under the curve (AUC) of DHM was 11.6±4.9 ng hr/mL. The results for this dosage form and amount are provided in Table 1, below. This result for the AUC based on this intravenous dosage was used in the bioavailability calculations discussed in Examples 2 and 3 and is summarized in Table 1, below.

Figure 2A:
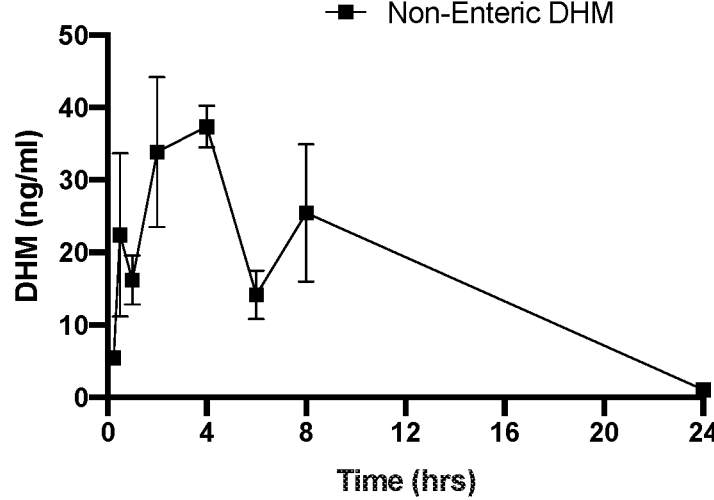
FIG. 2A presents the average blood concentration of dihydromyricetin (DHM) in ng/mL as a function of time in hours (hrs) following oral administration of an average of 79.1±1.3 mg of DHM per kg body weight to each rat in a set of rats. The DHM was administered in substantially crystalline form in non-enteric capsules. No sodium caprate (sodium decanoate) was administered. Error bars for each point in time based on the results for each of the rats in the set are shown. The maximum concentration $(C_{max})$ of DHM was 46.2±4.0 ng/mL at 4.7±1.8 hrs, and the area under the curve (AUC) of DHM was 313.6±114.9 ng hr/mL.

Example 2: Pharmacokinetic (PK) Data from Oral Administration of Dihydromyricetin (DHM) in Non-Enteric Capsules An average of 79.1±1.3 mg of dihydromyricetin (DHM) per kg body weight was orally administered to each rat in a set of three (3) Sprague-Dawley rats. The DHM was administered in substantially (or entirely) crystalline form in non-enteric capsules (hard gelatin, Torpac size 9 capsules). No sodium caprate (sodium decanoate) was administered;

i.e., the mass ratio of sodium caprate:DHM was 0:1. A blood sample was collected from each rat at predetermined times and analyzed with LC-MS/MS. FIG. 2A presents the average blood concentration of dihydromyricetin (DHM) in ng/mL as a function of time in hours (hrs) following administration. Error bars for each point in time based on the results for each of the rats in the set are shown. The maximum concentration ($C_{max}$) of DHM was 46.2±4.0 ng/mL at a time following administration ($T_{max}$) of 4.7±1.8 hrs, and the area under the curve (AUC) of DHM was 313.6±114.9 ng hr/mL. Bioavailability ($F_{abs}$) was calculated as $$F_{abs} = 100 \frac{AUC_{oral}/D_{oral}}{AUC_{IV}/D_{IV}}$$

where $AUC_{oral}$ and $D_{oral}$ indicate the AUC and dosage for a given oral administration, and $AUC_{IV}$ and $D_{IV}$ indicate the AUC and dosage for the intravenous (IV) administration set forth in Example 1, above. For the oral administration described here and shown in FIG. 2A, the bioavailability ($F_{abs}$) was 34.1±12.7. The results for this dosage form and amount are summarized in Table 1, below.

Figure 2B:
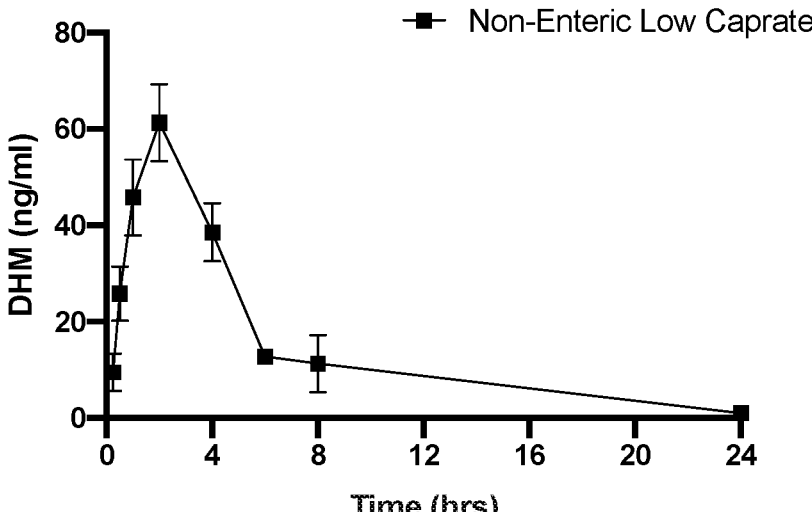
FIG. 2B presents the average blood concentration of dihydromyricetin (DHM) in ng/mL as a function of time in hours (hrs) following oral administration of an average of 93.9±1.4 mg of DHM per kg body weight to each rat in a set of rats. The DHM was administered in substantially crystalline form in non-enteric capsules. Sodium caprate (sodium decanoate) was administered in solid form within the non-enteric capsules at approximately 23.5 mg per kg body weight. Error bars for each point in time based on the results for each of the rats in the set are shown. The maximum concentration $(C_{max})$ of DHM was 61.3±8.0 ng/mL at 2.0±0 hrs, and the area under the curve (AUC) of DHM was 315.5±87 ng hr/mL.

An average of 93.9±1.4 mg of dihydromyricetin (DHM) per kg body weight was orally administered to each rat in a set of three (3) Sprague-Dawley rats. The DHM was administered in substantially crystalline form in non-enteric capsules. Sodium caprate (sodium decanoate) was administered in solid form within the non-enteric capsules at approximately 23.5 mg per kg body weight; i.e., the mass ratio of sodium caprate:DHM was 1:4. FIG. 2B presents the average blood concentration of dihydromyricetin (DHM) in ng/mL as a function of time in hours (hrs) following administration. Error bars for each point in time based on the results for each of the rats in the set are shown. The maximum concentration ($C_{max}$) of DHM was 61.3±8.0 ng/mL at a time following administration ($T_{max}$) of 2.0±0 hrs, and the area under the curve (AUC) of DHM was 315.5±87 ng hr/mL. For the oral administration described here and shown in FIG. 2B, the bioavailability ($F_{abs}$) was 28.8±7.8. The results for this dosage form and amount are summarized in Table 1, below.

Figure 2C:
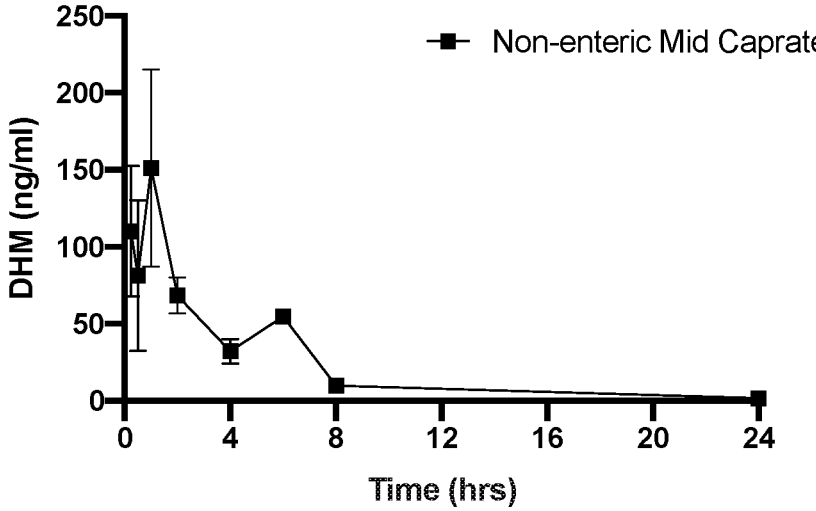
FIG. 2C presents the average blood concentration of dihydromyricetin (DHM) in ng/mL as a function of time in hours (hrs) following oral administration of an average of 76.5±1.7 mg of DHM per kg body weight to each rat in a set of rats. The DHM was administered in substantially crystalline form in non-enteric capsules. Sodium caprate (sodium decanoate) was administered in solid form within the non-enteric capsules at approximately 76.5 mg per kg body weight. Error bars for each point in time based on the results for each of the rats in the set are shown. The maximum concentration $(C_{max})$ of DHM was 191.8±44.8 ng/mL at 0.8±0.3 hrs, and the area under the curve (AUC) of DHM was 466.3±99.4 ng hr/mL.

An average of 76.5±1.7 mg of dihydromyricetin (DHM) per kg body weight was orally administered to each rat in a set of three (3) Sprague-Dawley rats. The DHM was administered in substantially crystalline form in non-enteric capsules. Sodium caprate (sodium decanoate) was administered in solid form within the non-enteric capsules at approximately 76.5 mg per kg body weight; i.e., the mass ratio of sodium caprate:DHM was 1:1. FIG. 2C presents the average blood concentration of dihydromyricetin (DHM) in ng/mL as a function of time in hours (hrs) following administration. Error bars for each point in time based on the results for each of the rats in the set are shown. The maximum concentration ($C_{max}$) of DHM was 191.8±44.8 ng/mL at a time following administration ($T_{max}$) of 0.8±0.3 hrs, and the area under the curve (AUC) of DHM was 466.3±99.4 ng hr/mL. For the oral administration described here and shown in FIG. 2C, the bioavailability ($F_{abs}$) was 52.8±12.3. The results for this dosage form and amount are summarized in Table 1, below.

Figure 2D:
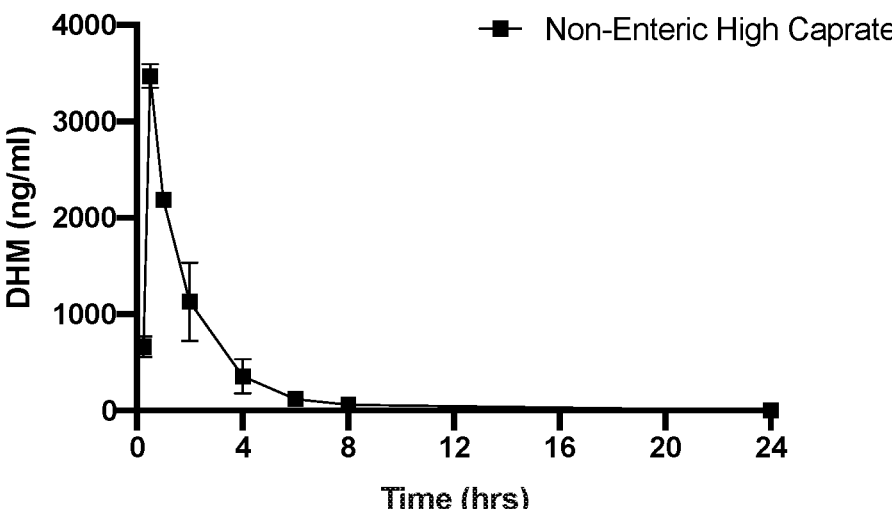
FIG. 2D presents the average blood concentration of dihydromyricetin (DHM) in ng/mL as a function of time in hours (hrs) following oral administration of an average of 77.5±1.7 mg of DHM per kg body weight to each rat in a set of rats. The DHM was administered in substantially crystalline form in non-enteric capsules. Sodium caprate (sodium decanoate) was administered in solid form within the non-enteric capsules at approximately 155 mg per kg body weight. Error bars for each point in time based on the results for each of the rats in the set are shown. The maximum concentration $(C_{max})$ of DHM was 3472.0±124.5 ng/mL at 0.5±0 hrs, and the area under the curve (AUC) of DHM was 5970.7±1424.3 ng hr/mL.

An average of 77.5±1.7 mg of dihydromyricetin (DHM) per kg body weight was orally administered to each rat in a set of three (3) Sprague-Dawley rats. The DHM was administered in substantially crystalline form in non-enteric capsules. Sodium caprate (sodium decanoate) was administered in solid form within the non-enteric capsules at approximately 155 mg per kg body weight; i.e., the mass ratio of sodium caprate:DHM was 2:1. FIG. 2D presents the average blood concentration of dihydromyricetin (DHM) in ng/mL as a function of time in hours (hrs) following administration. Error bars for each point in time based on the results for each of the rats in the set are shown. The maximum concentration ($C_{max}$) of DHM was 3472.0±124.5 ng/mL at a time following administration ($T_{max}$) of 0.5±0 hrs, and the area under the curve (AUC) of DHM was 5970.7±1424.3 ng hr/mL. For the oral administration described here and shown in FIG. 2D, the bioavailability ($F_{abs}$) was 662.2±157.9. The results for this dosage form and amount are summarized in Table 1, below.

A comparison of FIGS. 2A-2D and the data for $C_{max}$ and AUC shown in Table 1 indicates that as the amount of administered sodium caprate increased for a constant amount of DHM, the $C_{max}$ and AUC increased, suggesting that the sodium caprate functioned as a permeabilizer facilitating absorption of the DHM into the bloodstream. The bioavailability increased as the amount of caprate increased for sodium caprate:DHM mass ratios of 1:4, 1:1, and 2:1 (a constant amount of DHM was administered). There was a large increase in $C_{max}$ and AUC when the amount of sodium caprate was increased from 76.5 mg per kg rat body weight, a sodium caprate:DHM ratio of 1:1 (FIG. 2C), to 155 mg per kg rat body weight, a sodium caprate:DHM ratio of 2:1 (FIG. 2D). The $T_{max}$ decreased as the amount of administered sodium caprate increased (a constant amount of DHM was administered), consistent with the sodium caprate having functioned as a permeabilizer.

Figure 3A:
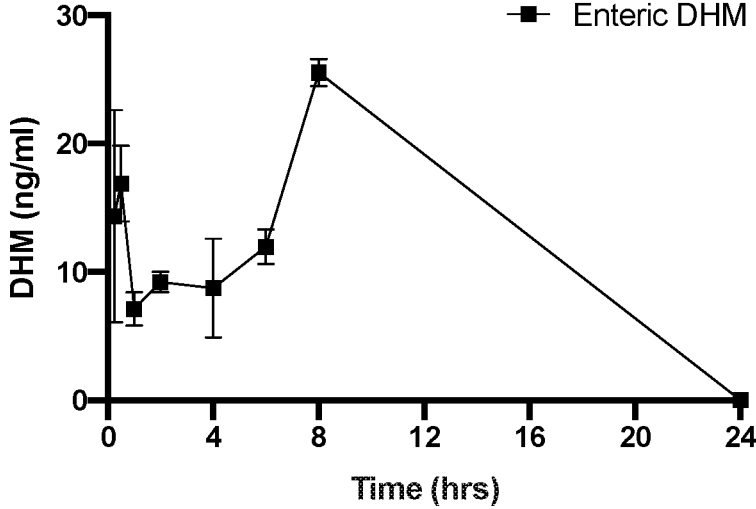
FIG. 3A presents the average blood concentration of dihydromyricetin (DHM) in ng/mL as a function of time in hours (hrs) following oral administration of an average of 73.1±1.1 mg of DHM per kg body weight to each rat in a set of rats. The DHM was administered in substantially crystalline form in enteric capsules. No sodium caprate (sodium decanoate) was administered. Error bars for each point in time based on the results for each of the rats in the set are shown. The maximum concentration $(C_{max})$ of DHM was 27.9±1.5 ng/mL at 5.4±2.6 hrs, and the area under the curve (AUC) of DHM was 167.3±83.3 ng hr/mL.

Example 3: Pharmacokinetic (PK) Data from Oral Administration of Dihydromyricetin (DHM) in Enteric Capsules An average of 73.1±1.1 mg of dihydromyricetin (DHM) per kg body weight was orally administered to each rat in a set of three (3) Sprague-Dawley rats. The DHM was administered in substantially (or entirely) crystalline form in enteric capsules (hard gelatin, Torpac size 9 capsules coated with Eudragit L100-55 (a poly(methacrylic acid-co-ethyl acrylate) copolymer which dissolves above pH 5.5)). No sodium caprate (sodium decanoate) was administered; i.e., the mass ratio of sodium caprate:DHM was 0:1. A blood sample was collected from each rat at predetermined times and analyzed with LC-MS/MS. FIG. 3A presents the average blood concentration of dihydromyricetin (DHM) in ng/ml as a function of time in hours (hrs) following administration. Error bars for each point in time based on the results for each of the rats in the set are shown. The maximum concentration ($C_{max}$) of DHM was 27.9±1.5 ng/mL at a time following administration ($T_{max}$) of 5.4±2.6 hrs, and the area under the curve (AUC) of DHM was 167.3+83.3 ng·hr/mL. Bioavailability ($F_{abs}$) was calculated as $$F_{abs} = 100 \frac{AUC_{oral}/D_{oral}}{AUC_{IV}/D_{IV}}$$

where $AUC_{oral}$ and $D_{oral}$ indicate the AUC and dosage for a given oral administration, and $AUC_{IV}$ and Dry indicate the AUC and dosage for the intravenous (IV) administration set forth in Example 1, above. For the oral administration described here and shown in FIG. 3A, the bioavailability ($F_{abs}$) was 19.5±9.5. The results for this dosage form and amount are summarized in Table 1, below.

Figure 3B:
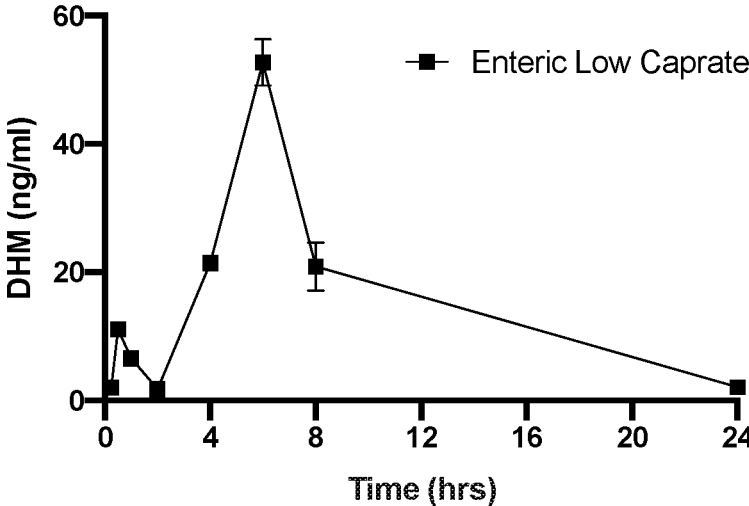
FIG. 3B presents the average blood concentration of dihydromyricetin (DHM) in ng/mL as a function of time in hours (hrs) following oral administration of an average of 92.6±3.0 mg of DHM per kg body weight to each rat in a set of rats. The DHM was administered in substantially crystalline form in enteric capsules. Sodium caprate (sodium decanoate) was administered in solid form within the non-enteric capsules at approximately 23.2 mg per kg body weight. Error bars for each point in time based on the results for each of the rats in the set are shown. The maximum concentration $(C_{max})$ of DHM was 52.7±3.6 ng/mL at 6.0±0 hrs, and the area under the curve (AUC) of DHM was 221.9±44.3 ng hr/mL.

An average of 92.6±3.0 mg of dihydromyricetin (DHM) per kg body weight was orally administered to each rat in a set of three (3) Sprague-Dawley rats. The DHM was administered in substantially crystalline form in enteric capsules. Sodium caprate (sodium decanoate) was administered in solid form within the enteric capsules at approximately 23.2 mg per kg body weight; i.e., the mass ratio of sodium caprate:DHM was 1:4. FIG. 3B presents the average blood concentration of dihydromyricetin (DHM) in ng/mL as a function of time in hours (hrs) following administration. Error bars for each point in time based on the results for each of the rats in the set are shown. The maximum concentration ($C_{max}$) of DHM was 52.7±3.6 ng/mL at a time following administration ($T_{max}$) of 6.0±0 hrs, and the area under the curve (AUC) of DHM was 221.9±44.3 ng hr/mL. For the oral administration described here and shown in FIG. 3B, the bioavailability ($F_{abs}$) was 20.4±3.6. The results for this dosage form and amount are summarized in Table 1, below.

Figure 3C:
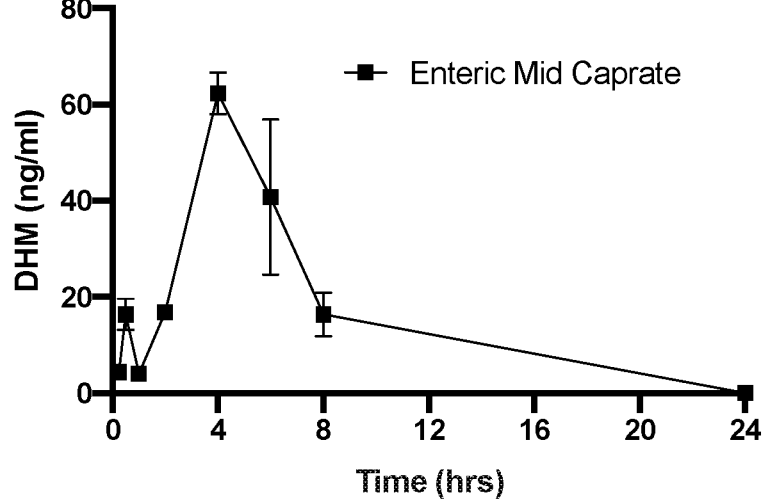
FIG. 3C presents the average blood concentration of dihydromyricetin (DHM) in ng/mL as a function of time in hours (hrs) following oral administration of an average of 75.5±2.0 mg of DHM per kg body weight to each rat in a set of rats. The DHM was administered in substantially crystalline form in enteric capsules. Sodium caprate (sodium decanoate) was administered in solid form within the non-enteric capsules at approximately 75.5 mg per kg body weight. Error bars for each point in time based on the results for each of the rats in the set are shown. The maximum concentration $(C_{max})$ of DHM was 62.3±4.3 ng/mL at 4.0±0 hrs, and the area under the curve (AUC) of DHM was 283.5±20.1 ng hr/mL.

An average of 75.5±2.0 mg of dihydromyricetin (DHM) per kg body weight was orally administered to each rat in a set of three (3) Sprague-Dawley rats. The DHM was administered in substantially crystalline form in non-enteric capsules. Sodium caprate (sodium decanoate) was administered in solid form within the non-enteric capsules at approximately 75.5 mg per kg body weight; i.e., the mass ratio of sodium caprate:DHM was 1:1. FIG. 3C presents the average blood concentration of dihydromyricetin (DHM) in ng/mL as a function of time in hours (hrs) following administration. Error bars for each point in time based on the results for each of the rats in the set are shown. The maximum concentration ($C_{max}$) of DHM was 62.3±4.3 ng/mL at a time following administration ($T_{max}$) of 4.0±0 hrs, and the area under the curve (AUC) of DHM was 283.5±20.1 ng hr/mL. For the oral administration described here and shown in FIG. 3C, the bioavailability ($F_{abs}$) was 32.4±3.1. The results for this dosage form and amount are summarized in Table 1, below.

Figure 3D:
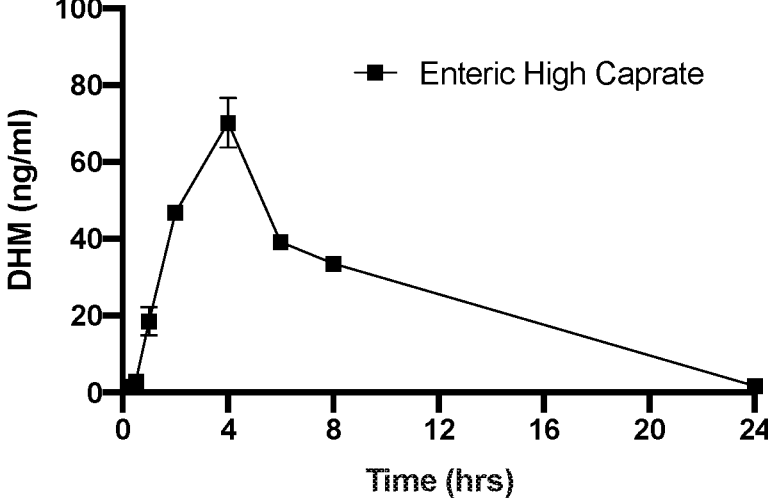
FIG. 3D presents the average blood concentration of dihydromyricetin (DHM) in ng/mL as a function of time in hours (hrs) following oral administration of an average of 70.6±2.7 mg of DHM per kg body weight to each rat in a set of rats. The DHM was administered in substantially crystalline form in enteric capsules. Sodium caprate (sodium decanoate) was administered in solid form within the non-enteric capsules at approximately 141.2 mg per kg body weight. Error bars for each point in time based on the results for each of the rats in the set are shown. The maximum concentration $(C_{max})$ of DHM was 70.2±6.5 ng/mL at 4.0±0 hrs, and the area under the curve (AUC) of DHM was 431.1±101.2 ng hr/mL.

An average of 70.6±2.7 mg of dihydromyricetin (DHM) per kg body weight was orally administered to each rat in a set of three (3) Sprague-Dawley rats. The DHM was administered in substantially crystalline form in non-enteric capsules. Sodium caprate (sodium decanoate) was administered in solid form within the non-enteric capsules at approximately 141.2 mg per kg body weight; i.e., the mass ratio of sodium caprate:DHM was 2:1. FIG. 3D presents the average blood concentration of dihydromyricetin (DHM) in ng/mL as a function of time in hours (hrs) following administration. Error bars for each point in time based on the results for each of the rats in the set are shown. The maximum concentration ($C_{max}$) of DHM was 70.2±6.5 ng/mL at a time following administration ($T_{max}$) of 4.0±0 hrs, and the area under the curve (AUC) of DHM was 431.1±101.2 ng hr/mL. For the oral administration described here and shown in FIG. 3C, the bioavailability ($F_{abs}$) was 51.7±10.0. The results for this dosage form and amount are summarized in Table 1, below.

A comparison of FIGS. 3A-3D and the data for $C_{max}$ and AUC shown in Table 1 indicates that as the amount of administered sodium caprate increased for a constant amount of DHM, the $C_{max}$ and AUC increased, suggesting that the sodium caprate functioned as a permeabilizer facilitating absorption of the DHM into the bloodstream. The bioavailability increased as the amount of administered sodium caprate increased for sodium caprate:DHM mass ratios of 0:1, 1:4, 1:1, and 2:1 (a constant amount of DHM was administered). The $T_{max}$ decreased as the amount of administered sodium caprate increased for sodium caprate:DHM mass ratios of 1:4 and 1:1 (a constant amount of DHM was administered), consistent with the sodium caprate having functioned as a permeabilizer.

TABLE 1

Pharmacokinetic data based on analysis of blood samples obtained from administration of dihydromyricetin (DHM) (and, in certain cases, sodium caprate) to Sprague-Dawley rats.

| Example | Fig. | Treatment | Na Caprate:DHM | DHM Dose (mg/kg) | DHM Cmax (ng/ml) | Tmax (hrs) | DHM AUC (ng · hr/mL) | DHM Bioavailability |
|---|---|---|---|---|---|---|---|---|
| 1 | 1 | DHM IV | | 1.0 | 12.5 ± 0.5 | | 11.6 ± 4.9 | |
| 2 | 2A | Non-enteric DHM Crystals | 0:1 | 79.1 ± 1.3 | 46.2 ± 4.0 | 4.7 ± 1.8 | 313.6 ± 114.9 | 34.1 ± 12.7 |
| | 2B | Non-enteric DHM Crystals + Caprate Low | 1:4 | 93.9 ± 1.4 | 61.3 ± 8.0 | 2.0 ± 0 | 315.5 ± 87 | 28.8 ± 7.8 |
| | 2C | Non-enteric DHM Crystals + Caprate Mid | 1:1 | 76.5 ± 1.7 | 191.8 ± 44.8 | 0.8 ± 0.3 | 466.3 ± 99.4 | 52.8 ± 12.3 |
| | 2D | Non-enteric DHM Crystals + Caprate High | 2:1 | 77.5 ± 1.7 | 3472.0 ± 124.5 | 0.5 ± 0 | 5970.7 ± 1424.3 | 662.2 ± 157.9 |
| 3 | 3A | Enteric DHM Crystals | 0:1 | 73.1 ± 1.1 | 27.9 ± 1.5 | 5.4 ± 2.6 | 167.3 ± 83.3 | 19.5 ± 9.5 |
| | 3B | Enteric DHM Crystals + Caprate Low | 1:4 | 92.6 ± 3.0 | 52.7 ± 3.6 | 6.0 ± 0 | 221.9 ± 44.3 | 20.4 ± 3.6 |
| | 3C | Enteric DHM Crystals + Caprate Mid | 1:1 | 75.5 ± 2.0 | 62.3 ± 4.3 | 4.0 ± 0 | 283.5 ± 20.1 | 32.4 ± 3.1 |
| | 3D | Enteric DHM Crystals + Caprate High | 2:1 | 70.6 ± 2.7 | 70.2 ± 6.5 | 4.0 ± 0 | 431.1 ± 101.2 | 51.7 ± 10.0 |

The average (mean) of a value is shown followed by the symbol ± and the standard error of the mean (SEM).

Example 4: Liquid Formulation Including DHM and Permeabilizer

An aqueous liquid formulation includes the following:
500 mg (or more) DHM;
1500 mg (or more) capric acid;
200 mg (or more) L-cysteine;
optionally prickly pear (extract);
optionally milk thistle (extract);
electrolyte(s) (e.g., sodium chloride, sodium citrate, and/ or potassium chloride);
vitamin(s) (e.g., one or more B vitamins, vitamin C, and/or vitamin E);
carbonation (carbon dioxide); and
optionally an emulsifier.

The aqueous liquid formulation can be of a volume of, for example, 4 oz (U.S customary fluid ounces) (118 mL), 8 oz (237 mL), 12 oz (355 mL), or 16 oz (474 mL). For example, the aqueous liquid formulation can be an oil-in-water emulsion (e.g., the water can be the continuous phase) or a water-in-oil emulsion (e.g., the oil can be the continuous phase). For example, the DHM can be (primarily) in the oil phase. For example, the permeabilizer (e.g., capric acid) can be (primarily) in the oil phase. For example, the aqueous liquid formulation of a volume of 4 oz can be a water-in-oil emulsion. For example, the aqueous liquid formulation of a volume of 8 oz, 12 oz, or 16 oz can be an oil-in-water emulsion. The aqueous liquid formulation of a given volume can be in a container (such as a sealable container for containing a beverage) of a corresponding volumetric capacity.

Aspects of the Invention

Aspect 1. A dihydromyricetin (DHM) formulation, comprising:
  dihydromyricetin (DHM) and
  a permeabilizer comprising a fatty acid salt and/or a fatty acid.
Aspect 2. The DHM formulation of Aspect 1, wherein the permeabilizer is a fatty acid salt.
Aspect 3. The DHM formulation of any one of Aspects 1 and 2, wherein the fatty acid salt is a sodium fatty acid salt or a potassium fatty acid salt.
Aspect 4. The DHM formulation of any one of Aspects 1 and 2, wherein the fatty acid salt is a saturated fatty acid salt.
Aspect 5. The DHM formulation of any one of Aspects 1 and 2, wherein the fatty acid salt is a sodium saturated fatty acid salt or a potassium saturated fatty acid salt.
Aspect 6. The DHM formulation of any one of Aspects 1 and 2, wherein the fatty acid salt is a sodium saturated fatty acid salt or a potassium saturated fatty acid salt having 8, 9, 10, 11, 12, 13, 14, 15, 16, 17, 18, 19, or 20 carbons.
Aspect 7. The DHM formulation of any one of Aspects 1 and 2, wherein the fatty acid salt is sodium decanoate (sodium caprate).
Aspect 8. The DHM formulation of any one of Aspects 1 and 2, wherein the fatty acid salt is potassium decanoate (potassium caprate).
Aspect 9. The DHM formulation of Aspect 1, wherein the permeabilizer is a fatty acid.
Aspect 10. The DHM formulation of any one of Aspects 1 through 9, wherein the fatty acid is a saturated fatty acid.

Aspect 11. The DHM formulation of any one of Aspects 1 through 9, wherein the fatty acid is a saturated fatty acid having 8, 9, 10, 11, 12, 13, 14, 15, 16, 17, 18, 19, or 20 carbons.
Aspect 12. The DHM formulation of any one of Aspects 1 through 9, wherein the fatty acid is a saturated fatty acid having 7, 8, 9, 10, 11, 12, or 13 carbons.
Aspect 13. The DHM formulation of any one of Aspects 1 through 9, wherein the fatty acid is decanoic acid (capric acid).
Aspect 14. The DHM formulation of any one of Aspects 1 through 9, wherein the fatty acid is in the form of a triglyceride.
Aspect 15. The DHM formulation of any one of Aspects 1 through 9, wherein the fatty acid is decanoic acid (capric acid) bonded to glycerol in a medium chain triglyceride.
Aspect 16. The DHM formulation of any one of Aspects 1 through 9, wherein the fatty acid is decanoic acid (capric acid) in a medium chain triglyceride formed of three decanoic acid (capric acid) groups bonded to glycerol.
Aspect 17. The DHM formulation of any one of Aspects 1 through 9,
  comprising a medium chain triglyceride formulation,
  wherein the medium chain triglyceride formulation comprises the fatty acid and
  wherein the fatty acid is decanoic acid (capric acid).
Aspect 18. The DHM formulation of any one of Aspects 1 through 9,
  comprising coconut oil,
  wherein the coconut oil comprises the fatty acid and
  wherein the fatty acid is decanoic acid (capric acid).
Aspect 19. The DHM formulation of any one of Aspects 1 through 9,
  comprising a natural product, a coconut product, palm kernel oil, palm oil, and/or durian extract,
  wherein the natural product, coconut product, palm kernel oil, palm oil, and/or durian extract comprises the fatty acid and
  wherein the fatty acid is decanoic acid (capric acid).
Aspect 20. The DHM formulation of any one of Aspects 1 through 19, comprising at least 1 mass unit of permeabilizer per mass unit of DHM.
Aspect 21. The DHM formulation of any one of Aspects 1 through 19, comprising at least 2 mass units of permeabilizer per mass unit of DHM.
Aspect 22. The DHM formulation of any one of Aspects 1 through 19, comprising at least 3 mass units of permeabilizer per mass unit of DHM.
Aspect 23. The DHM formulation of any one of Aspects 1 through 19, comprising from 1 to 2 mass units of permeabilizer per mass unit of DHM.
Aspect 24. The DHM formulation of any one of Aspects 1 through 19, comprising from 1 to 3 mass units of permeabilizer per mass unit of DHM.
Aspect 25. The DHM formulation of any one of Aspects 1 through 24, 146, and 147, wherein the DHM is in solid form.
Aspect 26. The DHM formulation of any one of Aspects 1 through 24, 146, and 147, wherein the DHM is in powder form.
Aspect 27. The DHM formulation of any one of Aspects 1 through 26, 146, and 147, wherein the DHM is crystalline.
Aspect 28. The DHM formulation of any one of Aspects 1 through 26, 146, and 147, wherein the crystallinity of the DHM is at least 90%.
Aspect 29. The DHM formulation of any one of Aspects 1 through 26, 146, and 147, wherein the crystallinity of the DHM is at least 80%.

Aspect 30. The DHM formulation of any one of Aspects 1 through 26, 146, and 147, wherein the crystallinity of the DHM is at least 50%.

Aspect 31. The DHM formulation of any one of Aspects 1 through 24, 146, and 147, wherein the DHM is solubilized or emulsified.

Aspect 32. The DHM formulation of any one of Aspects 1 through 31, 146, and 147, wherein the DHM formulation is homogeneous.

Aspect 33. A dosage form, comprising the DHM formulation of any one of Aspects 1 through 32, 146, and 147 as a tablet, caplet, pill, pastille, troche, or lozenge.

Aspect 34. A dosage form, comprising:
the dihydromyricetin (DHM) formulation of any one of Aspects 1 through 32, 146, and 147; and
a capsule,
wherein the DHM formulation is encapsulated in the capsule.

Aspect 35. The dosage form of Aspect 34, wherein the capsule is a soft gel capsule.

Aspect 36. The dosage form of Aspect 34 or 35, wherein the capsule comprises animal-derived material, such as gelatin and/or collagen.

Aspect 37. The dosage form of Aspect 34 or 35, wherein the capsule comprises plant-derived material.

Aspect 38. The dosage form of Aspect 34 or 35, wherein the capsule comprises synthetically-produced material.

Aspect 39. The dosage form of Aspect 34 or 35, wherein the capsule comprises a polysaccharide, a sulfated polysaccharide, a carrageenan, cellulose, a cellulose derivative, starch, a starch derivative, pullulan, polyvinyl alcohol (PVA), polyvinyl alcohol (PVA) copolymer, polyethylene glycol (PEG), and combinations.

Aspect 40. The dosage form of Aspect 34 or 35, wherein the capsule comprises hydroxypropyl methylcellulose (HPMC).

Aspect 41. The dosage form of Aspect 34 or 35, wherein the capsule comprises hydroxypropyl methyl cellulose acetate succinate (HPMCAS).

Aspect 42. The dosage form of Aspect 34 or 35, wherein the capsule comprises material of algal origin.

Aspect 43. The dosage form of Aspect 34 or 35, wherein the capsule comprises material derived from material of algal origin.

Aspect 44. The dosage form of any one of Aspects 33 through 43, wherein the dosage form comprises an exterior surface and wherein the exterior surface is coated with an enteric coating.

Aspect 45. The dosage form of Aspect 44, wherein the enteric coating is a polymeric coating.

Aspect 46. The dosage form of Aspect 44, wherein the enteric coating is a methacrylate copolymer coating.

Aspect 47. The dosage form of Aspect 44, wherein the enteric coating is poly(methacrylic acid-co-ethyl acrylate).

Aspect 48. The dosage form of any one of Aspects 33 through 47, wherein the dosage form is not solubilized or dissolved by an aqueous solution having a pH of at most 3.5.

Aspect 49. The dosage form of any one of Aspects 33 through 47, wherein the dosage form is not solubilized or dissolved by an aqueous solution having a pH of at most 2.

Aspect 50. The dosage form of any one of Aspects 33 through 47, wherein the dosage form is solubilized or dissolved by water or an aqueous solution having a pH of at least 5.5.

Aspect 51. The dosage form of any one of Aspects 33 through 47, wherein the dosage form is solubilized or dissolved by water or an aqueous solution having a pH of at least 7.

Aspect 52. A dosage form, comprising:
the dihydromyricetin (DHM) formulation of any one of Aspects 1 through 24, 31, 32, 146, and 147; and
a soft gel capsule,
wherein the DHM formulation is in liquid or gel form and wherein the DHM formulation is encapsulated in the soft gel capsule.

Aspect 53. A dosage form, comprising the DHM formulation of any one of Aspects 1 through 24, 31, 32, 146, and 147 in liquid or gel form.

Aspect 54. A dosage form, comprising:
the dihydromyricetin (DHM) formulation of any one of Aspects 1 through 24, 31, 32, 146, and 147,
wherein the DHM is dissolved, emulsified, dispersed as a suspension, or dispersed as a colloid in an aqueous liquid and
wherein the aqueous liquid comprises at least 0.04 wt % DHM.

Aspect 55. The dosage form of Aspect 54, wherein the aqueous liquid comprises at least 0.07 wt % DHM.

Aspect 56. The dosage form of Aspect 54, wherein the aqueous liquid comprises at least 0.1 wt % DHM.

Aspect 57. The dosage form of Aspect 54, wherein the aqueous liquid comprises at least 0.14 wt % DHM.

Aspect 58. The dosage form of Aspect 54, wherein the aqueous liquid comprises at least 0.2 wt % DHM.

Aspect 59. The dosage form of Aspect 54, wherein the aqueous liquid comprises at least 0.4 wt % DHM.

Aspect 60. The dosage form of Aspect 54, wherein the aqueous liquid comprises at least 1 wt % DHM.

Aspect 61. The dosage form of Aspect 54, wherein the aqueous liquid comprises at least 2, 3, or 4 wt % DHM.

Aspect 62. The dosage form of any one of Aspects 54 through 61, wherein the aqueous liquid further comprises cysteine.

Aspect 63. The dosage form of Aspect 62, wherein the aqueous liquid further comprises at least 0.02 wt % cysteine.

Aspect 64. The dosage form of Aspect 62, wherein the aqueous liquid comprises at least 0.05 wt % cysteine.

Aspect 65. The dosage form of Aspect 62, wherein the aqueous liquid comprises at least 0.1 wt % cysteine.

Aspect 66. The dosage form of Aspect 62, wherein the aqueous liquid comprises at least 0.2 wt % cysteine.

Aspect 67. The dosage form of any one of Aspects 54 through 66, wherein the aqueous liquid further comprises an emulsifier.

Aspect 68. The dosage form of Aspect 67, wherein the emulsifier is a plant product.

Aspect 69. The dosage form of Aspect 67, wherein the emulsifier is lecithin.

Aspect 70. The dosage form of any one of Aspects 54 through 69, wherein the aqueous liquid has a pH of at most 7.

Aspect 71. The dosage form of any one of Aspects 54 through 69, wherein the aqueous liquid has a pH of at most 5.

Aspect 72. The dosage form of any one of Aspects 54 through 71, wherein the aqueous liquid further comprises carbon dioxide.

Aspect 73. The dosage form of Aspect 72, wherein the aqueous liquid further comprises at least 0.1 wt % carbon dioxide.

Aspect 74. The dosage form of Aspect 72, wherein the aqueous liquid further comprises at least 0.5 wt % carbon dioxide.

Aspect 75. The dosage form of Aspect 72, wherein the aqueous liquid further comprises at least 0.8 wt % carbon dioxide.

Aspect 76. The dosage form of Aspect 72, wherein the aqueous liquid further comprises at least 1.5 wt % carbon dioxide.

Aspect 77. The dihydromyricetin (DHM) formulation of any one of Aspects 1 through 32, 146, and 147 or the dosage form according to any one of Aspects 33 through 76 and 132 through 145 for use as a medicament.

Aspect 78. The dihydromyricetin (DHM) formulation of any one of Aspects 1 through 32, 146, and 147 or the dosage form according to any one of Aspects 33 through 76 and 132 through 145 for use in reducing hangover symptoms.

Aspect 79. The dihydromyricetin (DHM) formulation of any one of Aspects 1 through 32, 146, and 147 or the dosage form according to any one of Aspects 33 through 76 and 132 through 145 for use in preventing an alcohol use disorder.

Aspect 80. The dihydromyricetin (DHM) formulation of any one of Aspects 1 through 32, 146, and 147 or the dosage form according to any one of Aspects 33 through 76 and 132 through 145 for use in preventing alcoholism.

Aspect 81. The dihydromyricetin (DHM) formulation of any one of Aspects 1 through 32, 146, and 147 or the dosage form according to any one of Aspects 33 through 76 and 132 through 145 for use in treating an alcohol use disorder.

Aspect 82. The dihydromyricetin (DHM) formulation of any one of Aspects 1 through 32, 146, and 147 or the dosage form according to any one of Aspects 33 through 76 and 132 through 145 for use in treating alcoholism.

Aspect 83. The dihydromyricetin (DHM) formulation of any one of Aspects 1 through 32, 146, and 147 or the dosage form according to any one of Aspects 33 through 76 and 132 through 145 for use in treating an alcohol overdose.

Aspect 84. The dihydromyricetin (DHM) formulation of any one of Aspects 1 through 32, 146, and 147 or the dosage form according to any one of Aspects 33 through 76 and 132 through 145 for use in increasing antioxidant capacity.

Aspect 85. The dihydromyricetin (DHM) formulation of any one of Aspects 1 through 32, 146, and 147 or the dosage form according to any one of Aspects 33 through 76 and 132 through 145 for use in neuroprotection.

Aspect 86. The dihydromyricetin (DHM) formulation of any one of Aspects 1 through 32, 146, and 147 or the dosage form according to any one of Aspects 33 through 76 and 132 through 145 for use in preventing Alzheimer's disease.

Aspect 87. The dihydromyricetin (DHM) formulation of any one of Aspects 1 through 32, 146, and 147 or the dosage form according to any one of Aspects 33 through 76 and 132 through 145 for use in treating Alzheimer's disease.

Aspect 88. The dihydromyricetin (DHM) formulation of any one of Aspects 1 through 32, 146, and 147 or the dosage form according to any one of Aspects 33 through 76 and 132 through 145 for use in inhibiting inflammation.

Aspect 89. The dihydromyricetin (DHM) formulation of any one of Aspects 1 through 32, 146, and 147 or the dosage form according to any one of Aspects 33 through 76 and 132 through 145 for use in protection of the kidney.

Aspect 90. The dihydromyricetin (DHM) formulation of any one of Aspects 1 through 32, 146, and 147 or the dosage form according to any one of Aspects 33 through 76 and 132 through 145 for use in protection of the liver.

Aspect 91. The dihydromyricetin (DHM) formulation of any one of Aspects 1 through 32, 146, and 147 or the dosage form according to any one of Aspects 33 through 76 and 132 through 145 for use in preventing or treating cancer.

Aspect 92. The dihydromyricetin (DHM) formulation of any one of Aspects 1 through 32, 146, and 147 or the dosage form according to any one of Aspects 33 through 76 and 132 through 145 for use in ameliorating a metabolic disorder.

Aspect 93. The dihydromyricetin (DHM) formulation of any one of Aspects 1 through 32, 146, and 147 or the dosage form according to any one of Aspects 33 through 76 and 132 through 145 for use in preventing diabetes.

Aspect 94. The dihydromyricetin (DHM) formulation of any one of Aspects 1 through 32, 146, and 147 or the dosage form according to any one of Aspects 33 through 76 and 132 through 145 for use in treating diabetes.

Aspect 95. The dihydromyricetin (DHM) formulation of any one of Aspects 1 through 32, 146, and 147 or the dosage form according to any one of Aspects 33 through 76 and 132 through 145 for use in treating a bacterial infection.

Aspect 96. The dihydromyricetin (DHM) formulation of any one of Aspects 1 through 32, 146, and 147 or the dosage form according to any one of Aspects 33 through 76 and 132 through 145 for use in treating depression, a depressive disorder, or major depressive disorder.

Aspect 97. Use of the dihydromyricetin (DHM) formulation of any one of Aspects 1 through 32, 146, and 147 in the manufacture of a medicament for reducing hangover symptoms.

Aspect 98. Use of the dihydromyricetin (DHM) formulation of any one of Aspects 1 through 32, 146, and 147 in the manufacture of a medicament for preventing an alcohol use disorder, preventing alcoholism, treating an alcohol use disorder, treating alcoholism, and/or treating an alcohol overdose.

Aspect 99. Use of the dihydromyricetin (DHM) formulation of any one of Aspects 1 through 32, 146, and 147 in the manufacture of a medicament for neuroprotection, preventing Alzheimer's disease, and/or treating Alzheimer's disease.

Aspect 100. Use of the dihydromyricetin (DHM) formulation of any one of Aspects 1 through 32, 146, and 147 in the manufacture of a medicament for ameliorating a metabolic disorder, preventing diabetes, and/or treating diabetes.

Aspect 101. Use of the dihydromyricetin (DHM) formulation of any one of Aspects 1 through 32, 146, and 147 in the manufacture of a medicament for increasing antioxidant capacity, inhibiting inflammation, protecting the kidney, protecting the liver, preventing and/or treating cancer, and/or treating a bacterial infection.

Aspect 102. Use of the dihydromyricetin (DHM) formulation of any one of Aspects 1 through 32, 146, and 147 in the manufacture of a medicament for treating depression, a depressive disorder, or major depressive disorder.

Aspect 103. A method for treating a patient suffering from a hangover symptom, comprising administering the dihydromyricetin (DHM) formulation of any one of Aspects 1 through 32, 146, and 147 or the dosage form according to any one of Aspects 33 through 76 and 132 through 145 to the patient to reduce the hangover symptom.

Aspect 104. A method for treating a patient at risk of an alcohol use disorder, comprising administering the dihydromyricetin (DHM) formulation of any one of Aspects 1 through 32, 146, and 147 or the dosage form according to any one of Aspects 33 through 76 and 132 through 145 to the patient to prevent the alcohol use disorder.

Aspect 105. A method for treating a patient at risk of alcoholism, comprising administering the dihydromyricetin (DHM) formulation of any one of Aspects 1 through 32, 146, and 147 or the dosage form according to any one of Aspects 33 through 76 and 132 through 145 to the patient to prevent the alcoholism.

Aspect 106. A method for treating a patient suffering from an alcohol use disorder, comprising administering the dihydromyricetin (DHM) formulation of any one of Aspects 1 through 32, 146, and 147 or the dosage form according to any one of Aspects 33 through 76 and 132 through 145 to the patient to treat the alcohol use disorder.

Aspect 107. A method for treating a patient suffering from alcoholism, comprising administering the dihydromyricetin (DHM) formulation of any one of Aspects 1 through 32, 146, and 147 or the dosage form according to any one of Aspects 33 through 76 and 132 through 145 to the patient to treat the alcoholism.

Aspect 108. A method for treating a patient suffering from an alcohol overdose, comprising administering the dihydromyricetin (DHM) formulation of any one of Aspects 1 through 32, 146, and 147 or the dosage form according to any one of Aspects 33 through 76 and 132 through 145 to the patient to treat the alcohol overdose.

Aspect 109. A method for treating a patient in need of increased antioxidant capacity, comprising administering the dihydromyricetin (DHM) formulation of any one of Aspects 1 through 32, 146, and 147 or the dosage form according to any one of Aspects 33 through 76 and 132 through 145 to the patient to increase the antioxidant capacity.

Aspect 110. A method for treating a patient in need of neuroprotection, comprising administering the dihydromyricetin (DHM) formulation of any one of Aspects 1 through 32, 146, and 147 or the dosage form according to any one of Aspects 33 through 76 and 132 through 145 to the patient to provide neuroprotection.

Aspect 111. A method for treating a patient at risk of Alzheimer's disease, comprising administering the dihydromyricetin (DHM) formulation of any one of Aspects 1 through 32, 146, and 147 or the dosage form according to any one of Aspects 33 through 76 and 132 through 145 to the patient to prevent Alzheimer's disease.

Aspect 112. A method for treating a patient suffering from Alzheimer's disease, comprising administering the dihydromyricetin (DHM) formulation of any one of Aspects 1 through 32, 146, and 147 or the dosage form according to any one of Aspects 33 through 76 and 132 through 145 to the patient to treat Alzheimer's disease.

Aspect 113. A method for treating a patient at risk of or suffering from inflammation, comprising administering the dihydromyricetin (DHM) formulation of any one of Aspects 1 through 32, 146, and 147 or the dosage form according to any one of Aspects 33 through 76 and 132 through 145 to the patient to inhibit the inflammation.

Aspect 114. A method for treating a patient in need of protection of the kidney, comprising administering the dihydromyricetin (DHM) formulation of any one of Aspects 1 through 32, 146, and 147 or the dosage form according to any one of Aspects 33 through 76 and 132 through 145 to the patient to protect the kidney.

Aspect 115. A method for treating a patient in need of protection of the liver, comprising administering the dihydromyricetin (DHM) formulation of any one of Aspects 1 through 32, 146, and 147 or the dosage form according to any one of Aspects 33 through 76 and 132 through 145 to the patient to protect the liver.

Aspect 116. A method for treating a patient at risk of or suffering from cancer, comprising administering the dihydromyricetin (DHM) formulation of any one of Aspects 1 through 32, 146, and 147 or the dosage form according to any one of Aspects 33 through 76 and 132 through 145 to the patient to prevent or treat the cancer.

Aspect 117. A method for treating a patient at risk of or suffering from a metabolic disorder, comprising administering the dihydromyricetin (DHM) formulation of any one of Aspects 1 through 32, 146, and 147 or the dosage form according to any one of Aspects 33 through 76 and 132 through 145 to the patient to prevent, treat, or ameliorate the metabolic disorder.

Aspect 118. A method for treating a patient at risk of diabetes, comprising administering the dihydromyricetin (DHM) formulation of any one of Aspects 1 through 32, 146, and 147 or the dosage form according to any one of Aspects 33 through 76 and 132 through 145 to the patient to prevent the diabetes.

Aspect 119. A method for treating a patient suffering from diabetes, comprising administering the dihydromyricetin (DHM) formulation of any one of Aspects 1 through 32, 146, and 147 or the dosage form according to any one of Aspects 33 through 76 and 132 through 145 to the patient to treat the diabetes.

Aspect 120. A method for treating a patient suffering from a bacterial infection, comprising administering the dihydromyricetin (DHM) formulation of any one of Aspects 1 through 32, 146, and 147 or the dosage form according to any one of Aspects 33 through 76 and 132 through 145 to the patient to treat the bacterial infection.

Aspect 121. A method for treating a patient suffering from depression, a depressive disorder, or major depressive disorder, comprising administering the dihydromyricetin (DHM) formulation of any one of Aspects 1 through 32, 146, and 147 or the dosage form according to any one of Aspects 33 through 76 and 132 through 145 to the patient to treat the depression, depressive disorder, or major depressive disorder.

Aspect 122. A method comprising administering the DHM formulation of any one of Aspects 1 through 32, 146, and 147 or the dosage form according to any one of Aspects 33 through 76 and 132 through 145 to a patient.

Aspect 123. The method of any one of Aspects 103 through 122, wherein the DHM is administered at a dose of from 5 mg to 150 mg DHM per kg patient body weight.

Aspect 124. The method of any one of Aspects 103 through 122, wherein the DHM is administered at a dose of from 50 mg to 100 mg DHM per kg patient body weight.

Aspect 125. The method of any one of Aspects 103 through 122, wherein the DHM is administered at a dose of about 75 mg DHM per kg patient body weight.

Aspect 126. The method of any one of Aspects 103 through 125, wherein the permeabilizer is administered at a dose of from 5 mg to 300 mg permeabilizer per kg patient body weight.

Aspect 127. The method of any one of Aspects 103 through 125, wherein the permeabilizer is administered at a dose of from 10 mg to 200 mg permeabilizer per kg patient body weight.

Aspect 128. The method of any one of Aspects 103 through 125, wherein the permeabilizer is administered at a dose of from 75 mg to 150 mg permeabilizer per kg patient body weight.

Aspect 129. The method of any one of Aspects 103 through 128, further comprising allowing the permeabilizer to permeabilize a wall of the patient's intestine and allowing the DHM to diffuse into the wall of the patient's intestine and into the patient's bloodstream, so that the DHM is administered to the patient. Aspect 130. The method of any one of Aspects 103 through 129, wherein the DHM formulation or the dosage form is administered orally.

Aspect 131. The method of Aspect 130, wherein the DHM formulation is administered as a capsule, and further comprising allowing the capsule to enter the patient's stomach, where the capsule is not dissolved and is not solubilized by gastric juices in the stomach, allowing the capsule to pass from the stomach to the patient's intestine, where the capsule is partially or fully dissolved or solubilized by intestinal fluid in the intestine, allowing the partially or fully dissolved or solubilized capsule to release the DHM formulation into the intestinal fluid, allowing the permeabilizer to permeabilize a wall of the patient's intestine, and allowing the DHM to diffuse into a wall of the intestine and into the patient's bloodstream, so that the DHM is administered to the patient.

Aspect 132. The dosage form of any one of Aspects 54 through 76, further comprising a water-soluble polymer.

Aspect 133. The dosage form of Aspect 132, wherein the water-soluble polymer is selected from the group consisting of poly(vinylpyrrolidone) (PVP) and poly(vinylpyrrolidone-co-vinyl acetate) (PVP-VA).

Aspect 134. The dosage form of Aspect 132, wherein the water-soluble polymer is selected from the group consisting of a cellulosic polymer, hydroxypropyl methylcellulose (HPMC), hydroxypropyl methylcellulose acetate succinate (HPMCAS), and carboxymethyl cellulose (CMC).

Aspect 135. The dosage form of any one of Aspects 54 through 76 and 132 through 134, further comprising a cyclodextrin.

Aspect 136. The dosage form of any one of Aspects 54 through 76 and 132 through 134, further comprising beta-cyclodextrin.

Aspect 137. A dosage form, comprising:

the dihydromyricetin (DHM) formulation of any one of Aspects 1 through 32, 146, and 147; and a matrix material.

Aspect 138. The dosage form of Aspect 137, wherein the matrix material is poly(ethylene oxide).

Aspect 139. The dosage form of Aspect 137, wherein the matrix material is a cellulosic polymer.

Aspect 140. The dosage form of Aspect 137, wherein the matrix material is hydroxypropyl methylcellulose (HPMC).

Aspect 141. The dosage form of Aspect 137, wherein the matrix material is hydroxypropyl methylcellulose acetate succinate (HPMCAS).

Aspect 142. The dosage form of Aspect 137, wherein the matrix material is poly(vinylpyrrolidone-co-vinyl acetate) (PVP-VA).

Aspect 143. The dosage form of Aspect 137, wherein the matrix material is poly(vinyl acetate-co-vinyl caprolactam-co-ethylene oxide).

Aspect 144. The dosage form of any one of Aspects 137 through 143, wherein the DHM and/or the permeabilizer is molecularly dispersed in the matrix material.

Aspect 145. The dosage form of any one of Aspects 137 through 144, wherein the DHM is amorphous.

Aspect 146. The DHM formulation of any one of Aspects 1 through 19, comprising at least 5 mass units of permeabilizer per mass unit of DHM. Aspect 147. The DHM formulation of any one of Aspects 1 through 19, comprising from 1 to 5 mass units of permeabilizer per mass unit of DHM.

The embodiments illustrated and discussed in this specification are intended only to teach those skilled in the art the best way known to the inventors to make and use the invention. Nothing in this specification should be considered as limiting the scope of the invention. All examples presented are representative and non-limiting. The above described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1. Powell, B. A. R., *COMPOSITIONS AND METHODS FOR PREVENTING AND RECOVERY FROMDETRI-MENTAL EFFECTS OF ALCOHOL CONSUMPTION*, U.S. Pat. No. 9,603,830, (Mar. 28, 2017), THRIVEPLUS LLC: USA.

2. Shen, Y., et al., *Dihydromyricetin As a Novel Anti-Alcohol Intoxication Medication*. The Journal of Neuroscience, 2012. 32(1): p. 390-401.

3. Breitenbach, J., *Melt extrusion: from process to drug delivery technology*. European Journal of Pharmaceutics and Biopharmaceutics, 2002. 54(2): p. 107-117.

4. Chokshi, R. and H. Zia, *Hot-melt extrusion technique: a review*. Iranian Journal of Pharmaceutical Research, 2010: p. 3-16.

5. Crowley, M. M., et al., *Pharmaceutical applications of hot-melt extrusion: part I*. Drug development and industrial pharmacy, 2007. 33(9): p. 909-926.

6. Maniruzzaman, M., et al., *A review of hot-melt extrusion: process technology to pharmaceutical products*. ISRN pharmaceutics, 2012. 2012.

7. Patil, H., R. V. Tiwari, and M. A. Repka, *Hot-Melt Extrusion: from Theory to Application in Pharmaceutical Formulation*. AAPS PharmSciTech, 2015. 17(1): p. 20-42.

8. Liang, J., R. Olsen, and I. Spigelman, *Methods of treating alcohol intoxication, alcohol use disorders, and alcohol abuse which comprise the administration of dihydromyricetin, in Google Patents*. 2012, The Regents of the University of California.

9. Thomson, J. E., J. John V. Landry, and M. W. Zembal, *HOT-MELT EXTRUSION COATING OF RANDOM COPOLYMER OF ETHYLENE AND MONO-CARBOX-YLIC ACID, in Google Patents*. 1966, The Dow Chemical Company: USA.

10. Schippers, H. and Remscheid-Lennep, *APPARATUS FOR HOT MELT EXTRUSION, in Google Patents*, U. PTO, Editor. 1968, Barmer Maschinenfabrik Aktieng-esellschaft Wupper tal-Oberbarmen, Germany.

11. McGinity, J. W. and F. Zhang, *Hot-melt extrudable pharmaceutical formulation in Google Patents*, U. PTO, Editor. 2002, University of Texas System: USA.

12. Miller, D. A., et al., *STABILIZED HME COMPOSITION WITH SMALL DRUG PARTICLES, in Google Patents*. 2008, BOARD OF REGENTS, THE UNIVERSITY OF TEXAS SYSTEM, Austin, TX (US): USA.

13. Alderman, D. A. and T. D. Wolford, *Sustained release dosage form based on highly plasticized cellulose ether gels, in Google Patents*. 1987, The Dow Chemical Company: USA.

14. Brough, C., et al., *THERMO-KINETIC MIXING FOR PHARMACEUTICAL APPLICATIONS*, in Google Patents. 2009, BOARD OF REGENTS, THE UNIVERSITY OF TEXAS SYSTEM, Austin, TX (US): USA.

15. Fischer, G., et al., *MATRIX COMPOSITIONS FOR CONTROLLED DELIVERY OF DRUG SUBSTANCES*, in Google Patents. 2007, EGALET A/S, Vaerlose (Denmark): USA.

16. Yang, R. K., et al., *UNIFORM FILMS FOR RAPID DISSOLVE DOSAGE FORM INCORPORATING TASTE-MASKING COMPOSITIONS*, in Google Patents. 2008, MONOSOLRX LLC, Portage, IN (US): USA.

17. Fuisz, R. C., et al., *POLYMER-BASED FILMS AND DRUG DELIVERY SYSTEMS MADE THEREFROM*, in Google Patents. 2007: USA.

18. Bernstein, H., et al., *MATRICES FORMED OF POLYMER AND HYDROPHOBIC COMPOUNDS FOR USE IN DRUG DELIVERY*, in Google Patents, U. PTO, Editor. 2004, Acusphere, Inc., Cambridge, MA (US): USA.

19. MacAllister, S. M., et al., *Pharmaceutical Formulation*, in Google Patents. 2004, SMITHKLINE BEECHAM CORPORATION.

20. McAllister, S. M., et al., *PHARMACEUTICAL FORMULATION*, in Google Patents. 2003, GLAXOSMITHKLINE.

21. Davies, D. L., et al., *Recent advances in the discovery and preclinical testing of novel compounds for the prevention and/or treatment of alcohol use disorders*. Alcoholism: Clinical and Experimental Research, 2013. 37(1): p. 8-15.

22. Liang, J., et al., *Dihydromyricetin prevents fetal alcohol exposure-induced behavioral and physiological deficits: the roles of GABA$_A$ receptors in adolescence*. Neurochemical research, 2014. 39(6): p. 1147-1161.

23. Shen, Y., et al., *Dihydromyricetin as a novel anti-alcohol intoxication medication*. Journal of Neuroscience, 2012. 32(1): p. 390-401.

24. Ji, Y., J. Li, and P. Yang, *Effects of fruits of Hovenia dulcis Thunb on acute alcohol toxicity in mice*. Zhong yao cai=Zhongyaocai=Journal of Chinese medicinal materials, 2001. 24(2): p. 126-128.

25. Fang, H. L., et al., *Treatment of chronic liver injuries in mice by oral administration of ethanolic extract of the fruit of Hovenia dulcis*. The American journal of Chinese medicine, 2007. 35(04): p. 693-703.

26. Hase, K., et al., *Hepatoprotective Effect of Hovenia dulcis THUNB. on Experimental Liver Injuries Induced by Carbon Tetrachloride or D-Galactosamine: Lipopolysaccharide*. Biological and pharmaceutical Bulletin, 1997. 20(4): p. 381-385.

27. Ji, Y., et al., *Effects of Hovenia dulcis Thunb on blood sugar and hepatic glycogen in diabetic mice*. Zhong yao cai=Zhongyaocai=Journal of Chinese medicinal materials, 2002. 25(3): p. 190-191.

28. Okuma, Y., et al., *Effect of extracts from Hovenia dulcis Thunb. alcohol concentration in rats and men administered alcohol*. Journal of Japanese Society of Nutrition and Food Science (Japan), 1995.

29. WANG, X.-y. and Z.-t. JIANG, *RESEARCH PROGRESS IN NATURAL ANTIOXIDANT DIHYDROMYRICETIN* [J]. Food Research and Development, 2007. 2: p. 056.

30. Zhang, X., et al., *Scavenging effect of dihydromyricetin on the free radicals by ESR*. Modern Food Science and Technology, 2010. 26(10): p. 1040-1042, 1070.

31. Liu, B., et al., *Characterization and antioxidant activity of dihydromyricetin-lecithin complex*. European Food Research and Technology, 2009. 230(2): p. 325-331.

32. Aungst, B. J., *Absorption enhancers: applications and advances*. The AAPS journal, 2012.14(1): p. 10-18.

33. Thanou, M., J. Verhoef, and H. Junginger, *Oral drug absorption enhancement by chitosan and its derivatives*. Advanced drug delivery reviews, 2001. 52(2): p. 117-126.

34. Whitehead, K., N. Karr, and S. Mitragotri, *Safe and effective permeation enhancers for oral drug delivery*. Pharmaceutical research, 2008. 25(8): p. 1782-1788.

35. Whitehead, K. and S. Mitragotri, *Mechanistic analysis of chemical permeation enhancers for oral drug delivery*. Pharmaceutical research, 2008. 25(6): p. 1412-1419.

36. Hu, J., K. P. Johnston, and R. O. Williams, *Nanoparticle Engineering Processes for Enhancing the Dissolution Rates of Poorly Water Soluble Drugs*. Drug development and industrial pharmacy, 2004. 30(3): p. 233-245.

37. Zhang, Y., et al., *Design and Solidification of Fast-Releasing Clofazimine Nanoparticles for Treatment of Cryptosporidiosis*. Molecular pharmaceutics, 2017. 14(10): p. 3480-3488.

38. Onoue, S., et al., *Self-micellizing solid dispersion of cyclosporine A with improved dissolution and oral bioavailability*. Eur J Pharm Sci, 2014. 62: p. 16-22.

The invention claimed is:

1. A dihydromyricetin (DHM) dosage form, comprising: crystalline DHM and a permeabilizer,
wherein the permeabilizer consists essentially of sodium caprate,
wherein there are 2 mass units of sodium caprate per mass unit of crystalline DHM, and
wherein the crystalline DHM and the permeabilizer are in a non-enteric capsule.

2. The DHM dosage form of claim 1, further comprising a matrix material.

3. A method for reducing a hangover symptom, comprising administering a therapeutically effective amount of the DHM dosage form of claim 1 to a patient in need of such reduction, thereby reducing the hangover symptom wherein the crystalline DHM is administered at a dose of from 5 mg to 150 mg crystalline DHM per kg patient body weight.

4. The method of claim 3, wherein the crystalline DHM is administered at a dose of from 50 mg to 100 mg crystalline DHM per kg patient body weight.

5. The method of claim 3, wherein the crystalline DHM is administered at a dose of about 75 mg crystalline DHM per kg patient body weight.

6. The method of claim 3, wherein the DHM dosage form is administered orally.

7. A method for treating an alcohol use disorder and/or alcoholism, comprising administering a therapeutically effective amount of the DHM dosage form of claim 1 to a patient in need of such treatment, thereby treating the alcohol use disorder and/or alcoholism wherein the crystalline DHM is administered at a dose of from 5 mg to 150 mg crystalline DHM per kg patient body weight.

8. A method for treating an alcohol overdose, comprising administering a therapeutically effective amount of the DHM dosage form of claim 1 to a patient in need of such treatment, thereby treating the alcohol overdose wherein the crystalline DHM is administered at a dose of from 5 mg to 150 mg crystalline DHM per kg patient body weight.

9. A method for increasing antioxidant capacity, inhibiting inflammation, providing neuroprotection, and/or treating Alzheimer's disease, comprising administering a therapeutically effective amount of the DHM dosage form of claim 1 to a patient in need of such increase, inhibition, provision, and/or treatment, thereby increasing the antioxidant capacity, inhibiting the inflammation, providing the neuroprotection, and/or treating the Alzheimer's disease wherein the crystalline DHM is administered at a dose of from 5 mg to 150 mg crystalline DHM per kg patient body weight.

10. A method for protecting the kidney, protecting the liver, treating cancer, ameliorating a metabolic disorder, treating diabetes, treating a bacterial infection, treating depression, treating a depressive disorder, and/or treating a major depressive disorder, comprising administering a therapeutically effective amount of the DHM dosage form of claim 1 to a patient in need of such protection, treatment, and/or amelioration, thereby protecting the kidney, protecting the liver, treating the cancer, ameliorating the metabolic disorder, treating the diabetes, treating the bacterial infection, treating the depression, treating the depressive disorder, and/or treating the major depressive disorder wherein the crystalline DHM is administered at a dose of from 5 mg to 150 mg crystalline DHM per kg patient body weight.

\* \* \* \* \*